United States Patent
Cui et al.

(10) Patent No.: US 8,830,573 B2
(45) Date of Patent: Sep. 9, 2014

(54) OPTICAL PHASE CONJUGATION 4PI MICROSCOPE

(75) Inventors: Meng Cui, Ashburn, VA (US); Changhuei Yang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 699 days.

(21) Appl. No.: 12/943,818

(22) Filed: Nov. 10, 2010

(65) Prior Publication Data
US 2011/0109962 A1    May 12, 2011

Related U.S. Application Data

(60) Provisional application No. 61/376,202, filed on Aug. 23, 2010, provisional application No. 61/355,328, filed on Jun. 16, 2010, provisional application No. 61/260,316, filed on Nov. 11, 2009, provisional application No. 61/259,975, filed on Nov. 10, 2009.

(51) Int. Cl.
*G02B 21/06* (2006.01)
*G02B 21/00* (2006.01)

(52) U.S. Cl.
CPC ........ *G02B 21/0056* (2013.01); *G02B 21/0068* (2013.01); *G02B 21/0092* (2013.01); *G02B 21/0004* (2013.01); *G02B 21/00* (2013.01)
USPC ........... 359/386; 359/368; 359/370; 359/371; 359/385

(58) Field of Classification Search
CPC ............... G02B 21/00; G02B 21/0056; G02B 21/0068; G02B 21/0092
USPC ................... 359/368–390, 237–298
See application file for complete search history.

(56) References Cited

U.S. PATENT DOCUMENTS

| | | | |
|---|---|---|---|
| 4,866,781 A | 9/1989 | Borken et al. | |
| 4,928,695 A | 5/1990 | Goldman et al. | |
| 5,671,085 A * | 9/1997 | Gustafsson et al. | 359/385 |
| 5,760,388 A | 6/1998 | Swandic | |
| 5,801,881 A * | 9/1998 | Lanni et al. | 359/386 |
| 7,081,994 B2 * | 7/2006 | Mueller et al. | 359/388 |
| 7,119,906 B2 * | 10/2006 | Pepper et al. | 356/484 |
| 8,450,674 B2 * | 5/2013 | Yang et al. | 250/208.1 |
| 2004/0027968 A1 * | 2/2004 | Horimai | 369/103 |
| 2010/0283835 A1 * | 11/2010 | Bewersdorf et al. | 348/47 |

OTHER PUBLICATIONS

Bilenca, A. et al., "Fluorescence coherence tomography," Optics Express 14, No. 16, Aug. 7, 2006, 7134.

(Continued)

*Primary Examiner* — Thong Nguyen
(74) *Attorney, Agent, or Firm* — Gates & Cooper LLP

(57) ABSTRACT

A 4-Pi microscope for imaging a sample, comprising a first objective for focusing a first light beam on the sample at a spatial point one or more Digital Optical Phase Conjugation (DOPC) devices, wherein the DOPC devices include a sensor for detecting the first light beam that has been transmitted through the sample and inputted on the sensor; and a spatial light modulator (SLM) for outputting, in response to the first light beam detected by the sensor, a second light beam that is an optical phase conjugate of the first light beam; and a second objective positioned to transmit the first light beam to the sensor and focus the second light beam on the sample at the spatial point, so that the first light beam and the second light beam are counter-propagating and both focused to the spatial point.

21 Claims, 18 Drawing Sheets

(56) References Cited

OTHER PUBLICATIONS

Boas, D. et al., "Imaging the body with diffuse optical tomography," IEEE Signal Processing, vol. 18, pp. 57-75, 2001.
Chalfie, M. et al., "Green fluorescent protein as a marker for gene expression," Science, vol. 263, Feb. 11, 1994, 802.
Cui, M. et al., "An in vivo study of turbidity suppression by optical phase conjugation (TSOPC) on rabbit ear," Optics Express 18, No. 1, Jan. 4, 2010, 25.
Cui, M. et al., "Implementation of a digital optical phase conjugation system and its application to study the robustness of turbidity suppression by phase conjugation," Optics Express 18, No. 4, Feb. 15, 2010, 3444.
Cui, M. et al., "Observation of polarization-gate based reconstruction quality improvement during the process of turbidity suppression by optical phase conjugation," Applied Physics Letters 95, 123702 (2009).
Cui, X. et al., "Lensless high-resolution on-chip optofluidic microscopes for *Caenorhabditis elegans* and cell imaging," PNAS, vol. 105, No. 31, Aug. 5, 2008, 10670-10675.
Debarre, D. et al., "Adaptive optics for structured illumination microscopy," Optics Express 16, No. 13, Jun. 23, 2008, 9290.
Debarre, D. et al., "Image-based adaptive optics for two-photo microscopy," Optics Letters, vol. 34, No. 16, Aug. 15, 2009, 2495.
Derode, A. et al., "Random multiple scattering of ultrasound. II. Is time reversal a self-averaging process?," Physical Review E, vol. 64, 2001, 036606.
Dougherty, T. et al., "Photodynamic therapy," Journal of the National Cancer Institute, vol. 90, No. 12, Jun. 17, 1998, 889.
Feinberg, J. et al., "Phase-conjugating mirror with continuous-wave gain," Optics Letters, vol. 5, No. 12, Dec. 1980, 519.
Feinberg, J. et al., "Photorefractive effects and light-induced charge migration in barium titanate," J. Appl. Phys. 51(3), Mar. 1980, 1297.
Fink, M., "Time reversed acoustics," Physics Today 50(3), 34-40 (1997).
Goodman, J., "Some fundamental properties of speckle," J. Opt. Soc. Am., vol. 66, No. 11, Nov. 1976, 1145.
Griffin, R. et al., "Use of a fluroescently labeled poly-casapase inhibitor for in vivo detection of apoptosis related to vascular-targeting agent arsenic trioxide for cancer therapy," Technology in Cancer Research and Treatment, vol. 6, No. 6, Dec. 2007, 651.
Hayden, E., "Microscopic marvels: Microscope for the masses," Nature, vol. 459, p. 632, 2009.
Hell, S. et al., "Fundamental improvement of resolution with a 4Pi-confocal fluorescence microscope using two-photon excitation," Optics Communications 93 (1992) 277-282.
Hell, S. et al., "Properties of a 4Pi confocal fluorescence microscope," J. Opt. Soc. Am. A, vol. 9, No. 12, Dec. 1992, 2159.
Hyde, S. et al., "Depth-resolved holography through turbid media using photorefraction," IEEE Journal of Selected Topics in Quantum Electronics, vol. 2, No. 4, Dec. 1996, 965.
Kawata, Y. et al., "4Pi confocal optical system with phase conjugation," Optics Letters 21, No. 18, Sep. 15, 1996, 1415.
Leith, E. et al,. "Holographic imagery through diffusing media," Journal of the Optical Society of America, vol. 56, No. 4, Apr. 1966, 523.
Lind, R. et al., "Demonstration of the longitudinal modes and aberration-correction properties of a continuous-wave dye laser with a phase-conjugate mirror," Optics Letters 6, No. 11, Nov. 1981, 554.
Lindsay, I., "Specular reflection cancellation/ enhancement in the presence of a phase-conjugate mirror," J. Opt. Soc. Am. B, vol. 4, No. 11, Nov. 1987, 1810.
McDowell, E. et al., "Turbidity suppression from the ballistic to the diffusive regime in biological tissues using optical phase," Journal of Biomedical Optics 15(2), 025004 (Mar./Apr. 2010).
Pepper, D., "Observation of diminished specular reflectivity from phase-conjugate mirrors," Physic Review Letters, vol. 62, No. 25, Jun. 19, 1989, 2945.
Primmerman, C. et al., "Compensation of atmospheric optical distortion using a synthetic beacon," Letters to Nature, vol. 353, Sep. 12, 1991, 141.
Ridley, K. et al., "Incomplete phase conjugation through a random phase screen. II. Numerical simulations," J. Opt. Soc. Am. A, vol. 13, No. 12, Dec. 1996, 2393.
Rueckel, M. et al., "Adaptive wavefront correction in two-photon microscopy using coherence-gated wavefront sensing," PNAS, vol. 103, No. 46, Nov. 14, 2006, 17137-17142.
Supatto, W. et al., "Quantitative imaging of collective cell migration during *Drosophila gastrulation* : multiphoton microscopy and computation analysis," Nature Protocols, vol. 4, No. 10, 2009, 1397.
Tsien, R., "The green fluorescent protein," Annu. Rev. Biochem. 1998, 67:509-44.
Vellekoop, I. et al., "Demixing light paths inside disordered metamaterials," Optics Express 16, No. 1, Jan. 7, 2008, 67.
Vellekoop, I. et al., "Focusing coherent light through opaque strongly scattering media," Optics Letters 32, No. 16, Aug. 15, 2007, 2309.
Vellekoop, I. et al., "Universal optical transmission of light through disordered materials," Physical Review Letters 101, 120601 (2008).
Wang, L., "Multiscale photoacoustic microscopy and computer tomography," Nature Photonics, vol. 3, Sep. 2009, 503.
Wang, L. et al., "Ultrasound-mediated biophotonic imaging: A review of acousto-optical tomography and photo-acoustic tomography," Disease Markers 19 (2003, 2004) 123-138.
Wang, L. et al., "Ultrasound-modulated optical tomography of absorbing objects buried in dense tissue-simulating turbid media," Applied Optics 36, No. 28, Oct. 1, 1997, 7277.
Wenner, M., "The most transparent research," Nat. Med. 15(10), 1106-1109 (2009).
Yamaguchi, I., "Phase-shifting digital holography," Optics Letters 22, No. 16, Aug. 15, 1997, 1268.
Yaqoob, Z. et al., "Optical phase conjugation for turbidity suppression in biological samples," Nature Photonics, vol. 2, Feb. 2008, 110.
Yariv, A., "Phase conjugate optics and real-time holography," IEEE Journal of Quantum Electronics, vol. QE-14, No. 9, Sep. 1978, 650.
Yuan, B. et al., "Ultrasound-modulated fluorescence from rhodamine B aqueous solution," Journal of Biomedical Optics 15(2), 021321 (Mar./Apr. 2010).
Zhang, T., "Three-dimensional microscopy with phase-shifting digital holography," Optics Letters 23, No. 15, Aug. 1, 1998, 1221.
Vo-Dinh, T., *Biomedical Photonics Handbook*, Boca Raton, Florida: CRC Press 2003, copyright and table of contents.
Yeh, P., *Introduction to Photorefractive Nonlinear Optics*, John Wiley & Sons, Inc., New York, 1993, copyright and table of contents.
Gower, D., *Optical Phase Conjugation* (Springer-Verlag, New York, 1994) copyright and table of contents.
Fink, M., "Time-reversed acoustics," Scientific American, vol. 28, pp. 91-97, Nov. 1999.

* cited by examiner

OPTICAL PHASE CONJUGATION 4PI MICROSCOPE

CROSS REFERENCE TO RELATED APPLICATIONS

This application claims the benefit under 35 U.S.C. 119(e) of the following co-pending and commonly-assigned U.S. provisional patent applications, which are incorporated by reference herein:

Provisional Patent Application Ser. No. 61/376,202, filed on Aug. 23, 2010, by Meng Cui and Changhuei Yang, entitled "OPTICAL PHASE CONJUGATION 4PI MICROSCOPE,";

Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY,";

Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES,"; and Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION,".

This application is related to the following co-pending and commonly-assigned U.S. patent applications, which are incorporated by reference herein:

U.S. Utility patent application Ser. No. 12/886,320, filed on Sep. 20, 2010, by Zahid Yaqoob, Emily McDowell and Changhuei Yang, entitled "OPTICAL PHASE PROCESSING IN A SCATTERING MEDIUM,", which application is a divisional of U.S. Utility patent application Ser. No. 11/868,394, filed on Oct. 5, 2007, by Zahid Yaqoob, Emily McDowell and Changhuei Yang, entitled "TURBIDITY ELIMINATION USING OPTICAL PHASE CONJUGATION AND ITS APPLICATIONS,", which application claims priority under 35 U.S.C. §119(e) to commonly-assigned U.S. Provisional Patent Application Ser. No. 60/850,356, filed on Oct. 6, 2006, by Zahid Yaqoob, Emily McDowell and Changhuei Yang, entitled "TURBIDITY ELIMINATION USING OPTICAL PHASE CONJUGATION AND ITS APPLICATIONS,";

U.S. Utility Application Ser. No. 12/943,857, filed on Nov. 19, 2010, by Chenghuei Yang and Meng Cui, entitled "TURBIDITY SUPPRESSION BY OPTICAL PHASE CONJUGATION USING A SPATIAL LIGHT MODULATOR,", which application claims priority under 35 U.S.C. §119(e) to and commonly-assigned U.S. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES,"; U.S. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION,"; U.S. Provisional Patent Application Ser. No. 61/376,202, filed on Aug. 23, 2010, by Meng Cui and Changhuei Yang, entitled "OPTICAL PHASE CONJUGATION 4PI MICROSCOPE,"; and U.S. Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY,"; and U.S. Utility application Ser. No. 12/943,841, filed on Nov. 10, 2010, by Meng Cui, Ying Min Wang, Chenghuei Yang and Charles DiMarzio, entitled "ACOUSTIC ASSISTED PHASE CONJUGATE OPTICAL TOMOGRAPHY,", which application claims priority under 35 U.S.C. §119(e) to and commonly-assigned U.S. Provisional Application Ser. No. 61/355,328, filed on Jun. 16, 2010, by Meng Cui, Ying Min Wang and Chenghuei Yang, entitled "ACOUSTIC ASSISTED PHASE CONJUGATE OPTICAL TOMOGRAPHY,"; U.S. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES,"; U.S. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION,"; and U.S. Provisional Patent Application Ser. No. 61/376,202, filed on Aug. 23, 2010, by Meng Cui and Changhuei Yang, entitled "OPTICAL PHASE CONJUGATION 4PI MICROSCOPE,".

BACKGROUND OF THE INVENTION

1. Field of the Invention

The present invention relates to 4-Pi microscopes.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

In this section, the present invention explains the concept and importance of 4pi fluorescence microscopy.

Microscopy is one of the most important tools in biomedical research. Over the past few decades, advanced optical imaging technologies have significantly expanded the capability of optical microscopy, providing high spatial resolution and molecular information. Among the various techniques, fluorescence micocopy provides excellent sensitivity and has gained its popularity among biologists since the introduction of a green fluorescence protein (GFP) [1, 2].

For three dimensional (3D) high resolution imaging, confocal microscopy is often used. With a pinhole at the focal plane rejecting the out-of-focus light, confocal microscopy can provide 3D images with ~600 nm axial resolution and ~200 nm lateral resolution.

The difference between the axial and the lateral resolution is associated to the angular distribution of the optical field of a single objective lens. FIG. 1 (a) shows the light intensity distribution at the focus of a Numerical Aperture (NA) 1.3 oil immersion objective lens illuminated by a collimated laser beam ($\lambda$=532 nm, filling factor=1). Even with such a high NA objective, the focus is still axially elongated, which can be understood by noting that the wave vectors of a single objective lens have components propagating to the left and the right along the lateral axis, but only a single direction (up or down) along the axial axis. The axial resolution can be significantly increased by adding a properly aligned opposing lens. The coherent addition of a second focus can create smaller excitation spots as shown in FIG. 1 (b). The imaging method employing two coherent opposing objective lenses in confocal fluorescence microscopy is known as 4Pi microscopy [3].

The resolution of confocal microscopy (including 4Pi) is determined by the product of excitation point spread function (PSF) and detection PSF, which gives rise to three different 4Pi systems (type A, B, and C) [3, 4].

In a type A 4Pi system, two excitation laser beams enter both objective lenses and the fluorescence signal exiting from one lens is used for confocal detection.

In a type B system, a single excitation beam enters one objective lens and the fluorescence signals exiting from both lenses are brought into coherent interference at the confocal detection system. Fluorescence emission is incoherent in that the emitted photons are uncorrelated. The interference effect employed in type B system is not between different photons but between the two different paths of a single emitted photon. Such an effect has also been employed for fluorescence OCT (optical coherence tomography) systems [5].

Type A and B systems can achieve similar spatial resolutions (axial ~120 nm, lateral ~200 nm). A further improvement on axial resolution can be made by combining type A and B systems such that two excitation beams enter both objective lenses and the fluorescence signals exiting both lenses are brought to interference at the confocal detection system, which is known as type C 4Pi system.

Despite the simple concept, the implementation of 4Pi microscope requires significant expertise in optics. Type A 4Pi may be used as an example to discuss some of the difficulties. First, to establish good interference between the two foci, the two opposing high NA (numerical aperture) oil immersion lenses need to be precisely aligned since inaccurate alignment can reduce the interference fringe contrast and lower the image quality. Second, the phase difference between the two excitation beams needs to be stabilized during the imaging process.

As can been see from FIG. 1 (c), the axial distribution of a 4Pi system comprises three peaks of the same width above the half maximum of intensity which means a single isolated fluorophore generates three images in an axial scan. The side peaks can be suppressed by multiplying the excitation PSF with the 4Pi detection PSF (type C 4Pi), by implementing two-photon excitation, and by using higher NA objectives such as Nikon Apo TIRF 60× NA 1.49 oil. The residue side peaks can be further removed mathematically with deconvolution algorithms. If the relative phase between the two excitation beams varies, the excitation PSF will be modified.

FIG. 1 (d) shows the scenario when the relative phase is changed by π. As expected, the peaks and valleys interchange as compared to FIG. 1 (b) and there are four peaks above half maximum as shown in FIG. 1 (e). If such a phase variation happens during imaging, the acquired image cannot be deconvoluted with a single axial distribution profile any more, resulting in image distortion. Experimentally, a compact and enclosed system is required to minimize the phase drift due to air current and mechanical perturbation, and phase stabilizing devices such as closed-loop piezo mirrors are often employed to improve the phase stability. Third, the imaged sample needs to be thin and optically homogeneous. Inhomogeneous region can cause aberration and distort the focus, altering the PSF.

Embodiments of the present invention use Optical Phase Conjugation (OPC) systems to solve the first (accurate alignment) and the third difficulties (optical aberration) of 4Pi microscopy. Specifically, a system is designed that is capable of automatic focus alignment and aberration compensation that permits using 4Pi microscopy for complex biological samples as embryos.

SUMMARY OF THE INVENTION

Scattering of light is the main obstacle preventing high resolution imaging through thick tissues. In order to overcome this limitation, and other limitations that will become apparent upon reading of this disclosure, one or more embodiments of the invention combine a Digital Optical Phase Conjugation (DOPC) with 4Pi microscopy to compensate the aberration caused by scattering in the path of one excitation beam.

The advantages of DOPC-4Pi are twofold. First, maintaining the precisely overlapped foci is of crucial importance to 4Pi microscopy. DOPC can ensure that the two excitation beams are phase conjugate to each other and their foci are automatically overlapped even when the relative position of the two objectives is changed due to mechanical instability, or a biological sample is inserted between the two objectives which causes aberration. Second, the wavefront distortion caused by scattering media can be compensated by DOPC. In such a way, 4Pi microscopy can be applied to more complicated samples such as *drosophila* embryos. However, a DOPC enabled 4Pi microscope may extend the imaging capability of 4Pi microscopy to even more complex cells and embryos.

A 4-Pi microscope provides the ability to image a sample, comprising a first objective for focusing a first light beam on the sample at a spatial point; one or more Digital Optical Phase Conjugation (DOPC) devices, wherein the DOPC devices include a sensor for detecting the first light beam that has been transmitted through the sample and inputted on the sensor; and a spatial light modulator (SLM) for outputting, in response to the first light beam detected by the sensor, a second light beam that is an optical phase conjugate of the first light beam; and a second objective positioned to transmit the first light beam to the sensor and focus the second light beam on the sample at the spatial point, so that the first light beam and the second light beam are counter-propagating and both focused to the spatial point.

The microscope may further comprise a sample holder, between the first objective and the second objective, for holding a sample such that the spatial point is on or within the sample, so that the first light beam is transmitted through the sample and the second objective before being collected by the DOPC devices.

The microscope may further comprise a source of an input reference beam, positioned to illuminate one or more pixels of the SLM, wherein the second light beam is a reflection of the input reference beam off the pixels of the SLM, and the pixels are for modulating the reference beam to create the optical phase conjugate.

The microscope may further comprise a beam splitter positioned to direct the first light beam, and transmit a sensor reference beam, to the sensor so that the first light beam and the sensor reference beam interfere and form one or more holograms on the sensor, the holograms including interferometric data. The microscope may further comprise an electro-optic modulator positioned to control a relative phase between the first light beam and the sensor reference beam, so that the holograms include one or more phase shifted holograms.

The microscope may further comprise one or more processors for receiving the interferometric data and determining one or more phases and one or more amplitudes of first light fields of the first light beam from the interferometric data, digitally modifying the phases and the amplitudes to produce one or more modified phases and one or more modified amplitudes, and outputting the modified phases and modified amplitudes to the SLM so that the SLM outputs the second light beam having the modified phases and modified amplitudes that are the optical phase conjugates of the phases and the amplitudes.

The microscope may further comprise a source for the input reference beam; and a computer processor and/or filter for controlling a power of the input reference beam so that the second light beam and the first light beam at the spatial point have identical powers as measured by maximum phase contrast in an interference pattern formed at the spatial point between the first light beam and the second light beam, or as measured by the first light beam and the second light beam independently generating an identical fluorescence signal.

The first light beam and the second light beam may have a power at the spatial point which is sufficiently low to avoid photobleaching of the sample at the spatial point, thereby optimizing fluorescence generated by exciting the sample at the spatial point with the first light beam and the second light beam.

The microscope may further comprise a detector positioned for imaging fluorescence of the sample generated by the first light beam and the second light beam.

The microscope may further comprise a laser that is the source for the input reference beam and a source for the first light beam, wherein the first light beam and the second light beam have a wavelength such that the fluorescence is generated by two photon excitation of the sample by the first light beam and the second light beam.

The DOPC devices may each have a response time or update speed of at least 1 KHz.

Embodiments of the invention further provide a method for imaging a sample using a 4-Pi Microscope, comprising focusing a first light beam at a spatial point on a sample; detecting the first light beam that has been transmitted through the sample, and outputting, using a spatial light modulator (SLM), a second light beam that is an optical phase conjugate of the first light beam, wherein the first light beam and the second light beam are counterpropagating and the second light beam retraces a path of the first light beam, thereby automatically aligning the 4-pi microscope; focusing the second light beam, or allowing the second light beam to focus, on the sample at the spatial point; using the first light beam and the second light beam to excite fluorescence from the sample at the spatial point; and using the fluorescence to image the sample.

A method further provides the ability to combine DOPC with a 4Pi confocal fluorescence microscope to characterize the microscope's spatial resolution.

A method also performs automatic focus alignment which can greatly simplify the operation of a 4Pi microscope and reduce the alignment error due to laser pointing instability and mechanical instability.

In addition, a method measures the aberration compensation capability of DOPC-4Pi system, using tissue phantoms to quantitatively determine the aberration compensation limit.

Embodiments of the present invention further provide a method of using a femtosecond laser to perform two-photon DOPC-4Pi microscopy.

Further, improved axial resolution may be obtained for imaging *drosophila* embryos.

BRIEF DESCRIPTION OF THE DRAWINGS

Referring now to the drawings in which like reference numbers represent corresponding parts throughout:

FIG. 1(b) shows coherent addition of an identical focus by an opposing lens (4Pi microscopy), FIG. 1(c) shows a comparison of the axial light intensity distribution in (a) and (b), FIG. 1 (d) shows the focus when the phase of one excitation beam is shifted by π, and FIG. 1(e) shows a comparison of the axial intensity distribution between (a) and (d);

FIG. 5(c) illustrates Tissue Suppression by Optical Phase Conjugation (TSOPC) transmission, and FIG. 5 (d) shows degradation of TSOPC transmission when the sample is shifted;

DETAILED DESCRIPTION OF THE INVENTION

Figure 1:
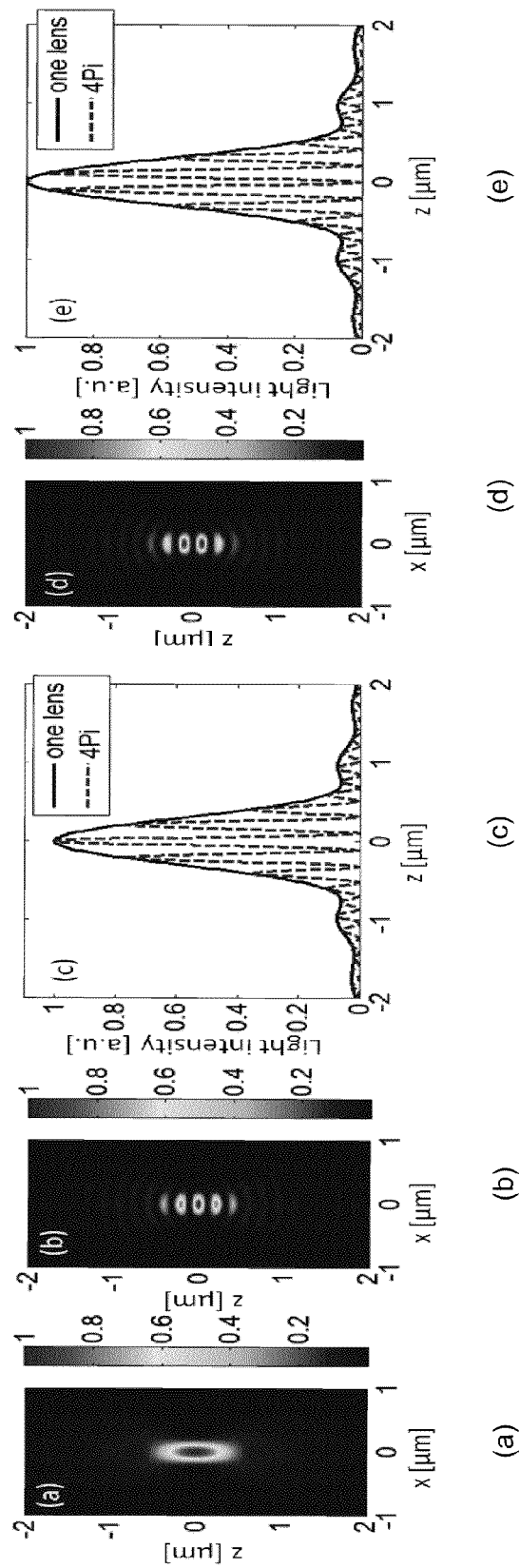
FIG. 1 (a) shows light intensity distribution at the focus of a NA1.3 objective illuminated by a CW laser (λ=532 nm) with filling factor=1.

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Overview

Embodiments of the present invention involve the adaptation of the TSOPC effect to improve and simplify a high-resolution 3D microscopy method known as 4Pi microscopy [15]. 4Pi microscopy is an imaging method in which two counter-propagating laser beams are tightly focused onto the same spatial spot. By raster-scanning this mutual focal spot over a sample and collecting the generated fluorescence signal from fluorophores excited within this focal spot, a high-resolution image of the sample may be rendered.

The lateral resolution of such a system is defined by the focal spot diameter. The two counter-propagating light beams mutually interfere along the axial direction. The resulting axial standing interference pattern and the point spread function of the focal spot define the axial resolution.

The mutual interference of the two beams allows a higher axial resolution than the confocal microscope system, e.g., an improvement in the axial resolution by a factor of 5-7 versus a standard confocal microscope using one or more of the embodiments of the present invention's digitally optical phase conjugation (DOPC)-assisted 4-Pi microscope. For example, the lateral and axial resolution of the 4-Pi microscope may be as high as 200 nm and 120 nm, respectively. In comparison, the more commonly used confocal microscope system typically has an axial resolution of 600 nm.

However, a conventional 4Pi microscope performs poorly for optically inhomogeneous samples as extensive scattering degrades the focal spot quality and can lead to a misalignment of the two focal spots. Furthermore, 4Pi microscopes are generally difficult to implement and use well because the exact superposition of the laser beams' focal spots is critical and easily disrupted.

Despite its resolution advantage over confocal microscopy, 4Pi microscopy is seldom used because the foci of the two beams need to be precisely aligned to each other. The usage of 4Pi microscopy is also restrictive for two reasons. First, bulk refractive index variations of a sample can deflect and misalign the two propagating beams—a good 4Pi microscope system must constantly correct for such misalignment during imaging. Second, tissue scattering can significantly distort one or both of the laser beams and prevent the forming of a good focal spot. This actually limits the tissue thickness that can be used with 4Pi microscopy.

The self-correcting nature of the TSOPC effect, as implemented by embodiments of the present invention, may be used to address these two weaknesses. Embodiments of the present invention provide a DOPC 4Pi microscope that is capable of high lateral (200 nm) and axial (120 nm) resolution imaging.

OPC may be roughly interpreted as the time-reversed playback of a target light field. Because scattering is deterministic, it is possible to undo tissue scattering by time-reversing a scattered light field through the target tissue. The incorporation of a specially adapted OPC arrangement in a 4Pi microscope allows such a microscope to adaptively align its focus and to correct sample aberration which has been an obstacle for conventional 4pi system.

The DOPC 4-Pi system may be used to obtain improved imaging of the *Drosophila* embryo, for example, an important model in developmental biology.

An OPC beam shaper may also be adapted into a 4Pi microscope system, wherein the target system resolution is 120 nm (axial) and 200 nm (lateral). The foci of the two excitation beams may then be automatically overlapped. The system's aberration compensation ability may be diagnosed with the help of tissue phantom sections.

A femtosecond laser source (e.g., 80 fs pulses) may be employed to demonstrate two-photon DOPC-4Pi system.

The application range of the DOPC 4Pi microscope is potentially broad. The aberration compensation ability allows this system to image thicker and heterogeneous samples. Such systems may be useful in neuroscience and developmental biology experiments where precise 3D mapping of complex samples, such as embryos, are important.

Technical Description

Optical Phase Conjugation

Figure 2:
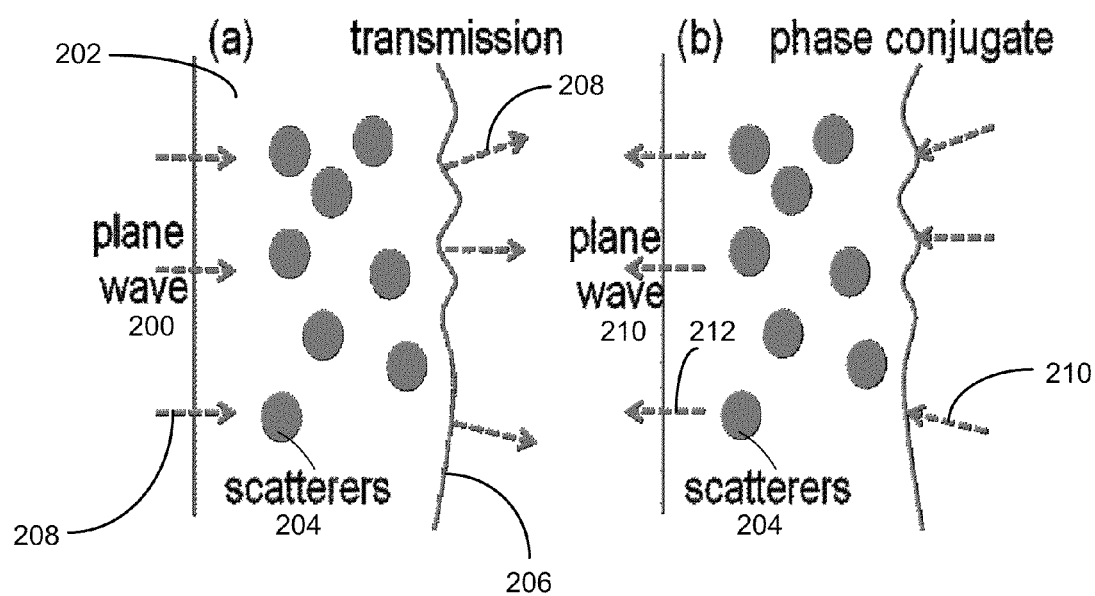
FIG. 2 illustrates the principle of OPC, wherein in FIG. 2(a), a plane wave travels through a scattering medium and the wavefront is distorted by scatterers, and in FIG. 2(b) the phase and the propagation direction of the transmitted wave is reversed and the initial input wavefront is recovered.

OPC has been an active research field since the 1970's and has generated numerous applications such as laser cavity aberration compensation, high resolution image projectors, and novel resonators [6-9]. The principle of OPC is illustrated in FIG. 2(a)-(b). In FIG. 2(a), a plane wave 200 travels through a random scattering medium 202 comprising scatterers 204. The transmitted wavefront 206 is distorted by the scatterers 204. If the propagation direction 208 and the phase of the transmitted wave are both reversed, the resulting wave can retrace the scattering path and reproduce the plane wave 210 with the opposite propagation direction 212, as shown in FIG. 2 (b).

Such a technique may also be applied to biological tissues through a holographic recording of the transmitted light in a photorefractive crystal followed by a time reversed playback. This effect, termed TSOPC [10], is surprisingly robust. The input wavefront can be reconstructed with high quality through 7 mm thick chicken tissue sections at a wavelength of 532 nm [11]. The biological samples that may be imaged with the novel 4Pi system are 100-200 microns thick, as limited by the working distance of water or oil immersion objectives. The optical aberration caused by such samples is significantly less than the 10 mm thick chicken tissue and is easy to compensate.

At this point, it is worth revisiting the topic of TSOPC and imaging. TSOPC does not literally turn tissue transparent. However, the TSOPC effect may be used to suppress scattering effects that plague existing optical imaging techniques, and thereby improve their performance. The OPC 4Pi microscopy method of embodiments of the invention is a good example. On a different front, the TSOPC effect may also be adapted to create entirely new classes of imaging systems.

OPC-4Pi System

Figure 3:
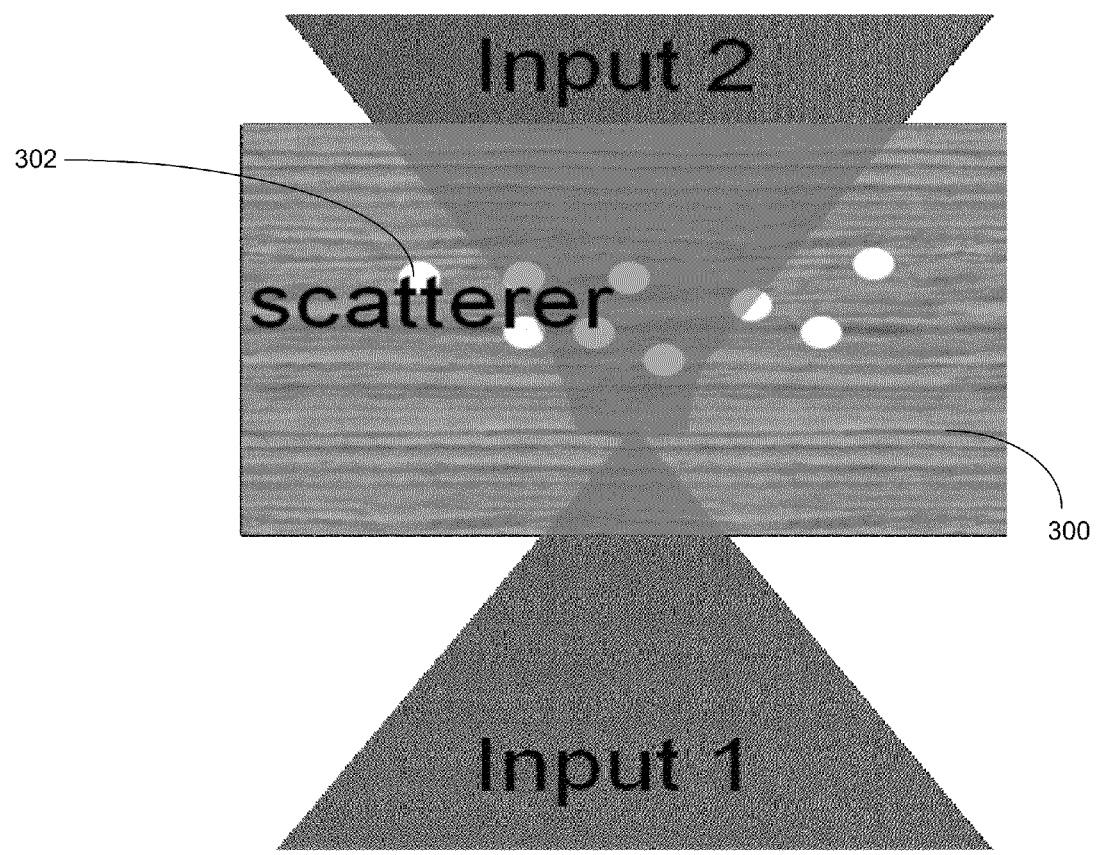
FIG. 3 illustrates how the presence of scatterers in the path of the input 2 beam distorts the focus and prevents the application of 4Pi microscopy.

The application of 4Pi microcopy has been limited to highly transparent and optical homogeneous media. For complex samples, the inhomogeneity inside the sample can cause severe focus distortion and prevent the application of 4Pi microscopy for high resolution imaging, as illustrated in FIG. 3. The technique of OPC is combined with a 4Pi system to solve such problems.

In FIG. 3 the upper beam (Input 2) travels through an aberration layer 300 comprising scatterers 302 and becomes distorted. If the Input 2 is blocked but lets a lower beam (Input 1) travel through the aberration layer and use its phase conjugate as Input 2, the focus distortion may be avoided. With the help of OPC, high resolution 4Pi microscopy can be applied to more complex samples. Such a solution may increase axial resolution by a factor of 5 as compared to conventional confocal microscopy.

The techniques for generating an OPC field have been well established. To adapt the existing technologies to 4Pi microscopy, three requirements have to be met:

1) The power of the phase conjugate signal has to be matched to that of the input power. Otherwise, the fringe contrast at the common focus of the input beam and the phase conjugate beam may be low, resulting in poor image quality;

2) The OPC system needs to be able to work with weak light power. For confocal fluorescence microscopy, the excitation power is often limited to below 1 mW for avoiding sample damage and reducing photobleaching rate; and 3) The OPC system should be able to work with a broad range of wavelengths for exciting different fluorophores.

A DOPC system may meet all three requirements and also has the flexibility of working with either continuous wave (CW) lasers or pulsed lasers, and, as such, the system may be used for either one photon or two photon fluorescence imaging.

Figure 4:
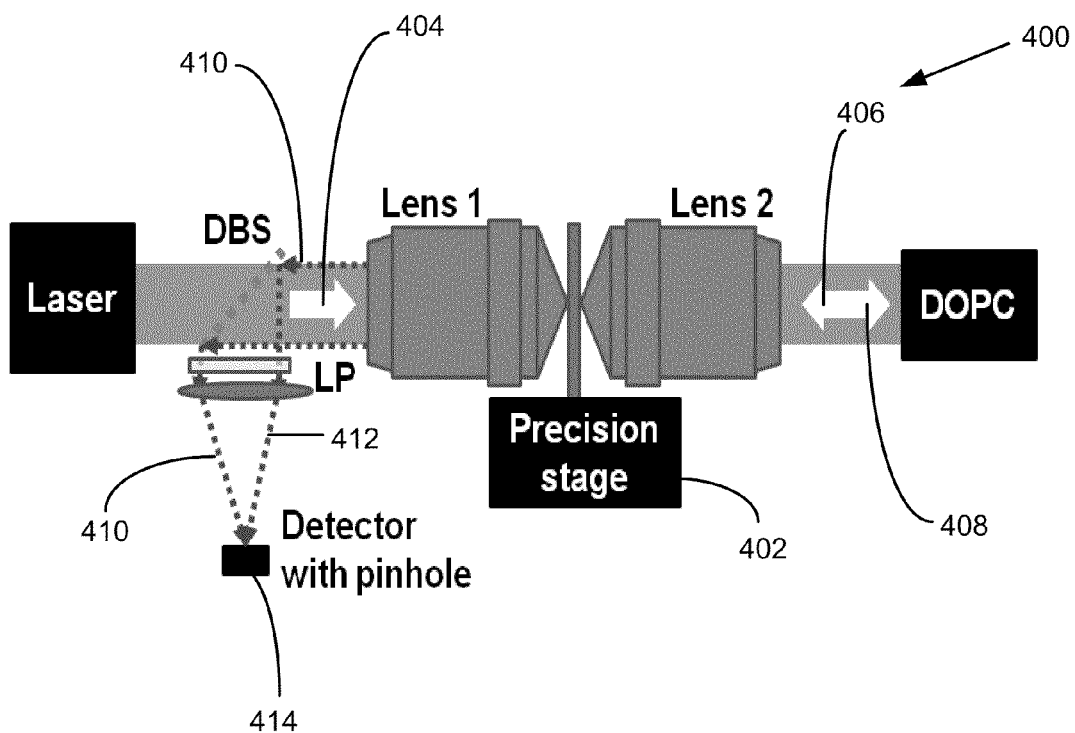
FIG. 4 illustrates a proposed DOPC-4Pi system, comprising dichroic beam splitter (DBS) and long-pass filter (LP), according to one or more embodiments of the present invention.

FIG. 4 is the schematic illustration of an OPC-4Pi system 400 according to one embodiment of the present invention. The sample is mounted on a closed loop piezo stage or precision stage 402 (PI, P-545.3R2) and is sandwiched between two oil immersion objective lenses, Lens 1 and Lens 2 (e.g., Nikon Apo TIRF 60× NA 1.49 oil). A collimated laser beam 404 enters the 4Pi system from one objective lens (Lens 1) and its transmission 406 through both objective lenses is collected by the DOPC system, DOPC. To generate the phase conjugate wave 408, the DOPC system first measures both the amplitude and the phase of the transmitted beam's 406 wavefront and then generates the phase conjugate wave 408 with a high speed spatial light modulator (SLM). In such a way, the generation of the OPC wave 408 is achieved through the wavefront measurement and modulation instead of using nonlinear optics. The advantage of DOPC is that the power of the OPC wave 408 can be easily adjusted by controlling the input power to the SLM and the same system can be used with either pulsed lasers or CW lasers of various wavelengths and power levels.

Embodiments of the present invention may combine two-photon type A 4Pi system with a DOPC, for example. The fluorescence signal 410 exiting from one lens (lens 1) is directed by a dichroic beam splitter (DBS) to a long-pass filter (LP) to reject the excitation light. The transmitted fluorescence signal 410 is focused 412 onto a pinhole and collected by an avalanche photodiode detector, or detector with pinhole 414. The aberration compensation capability of the DOPC-4Pi system may be characterized with tissue phantoms and the DOPC-4Pi may be applied to image *drosophila* embryos, for example.

Potential Merit Requirements for the OPC-4Pi System

In the next sections, the theory and implementation of OPC as applied to the OPC-4Pi system is described. Specifically, three preliminary experiments are described, wherein, in the first experiment, TSOPC is observed through chicken tissue sections; in the second experiment, the experimental results of observing TSOPC through live rabbit ear are described; and in the third experiment, the new type of OPC system, digital OPC (DOPC) is introduced.

TSOPC Through Chicken Tissue Sections

Figure 5:
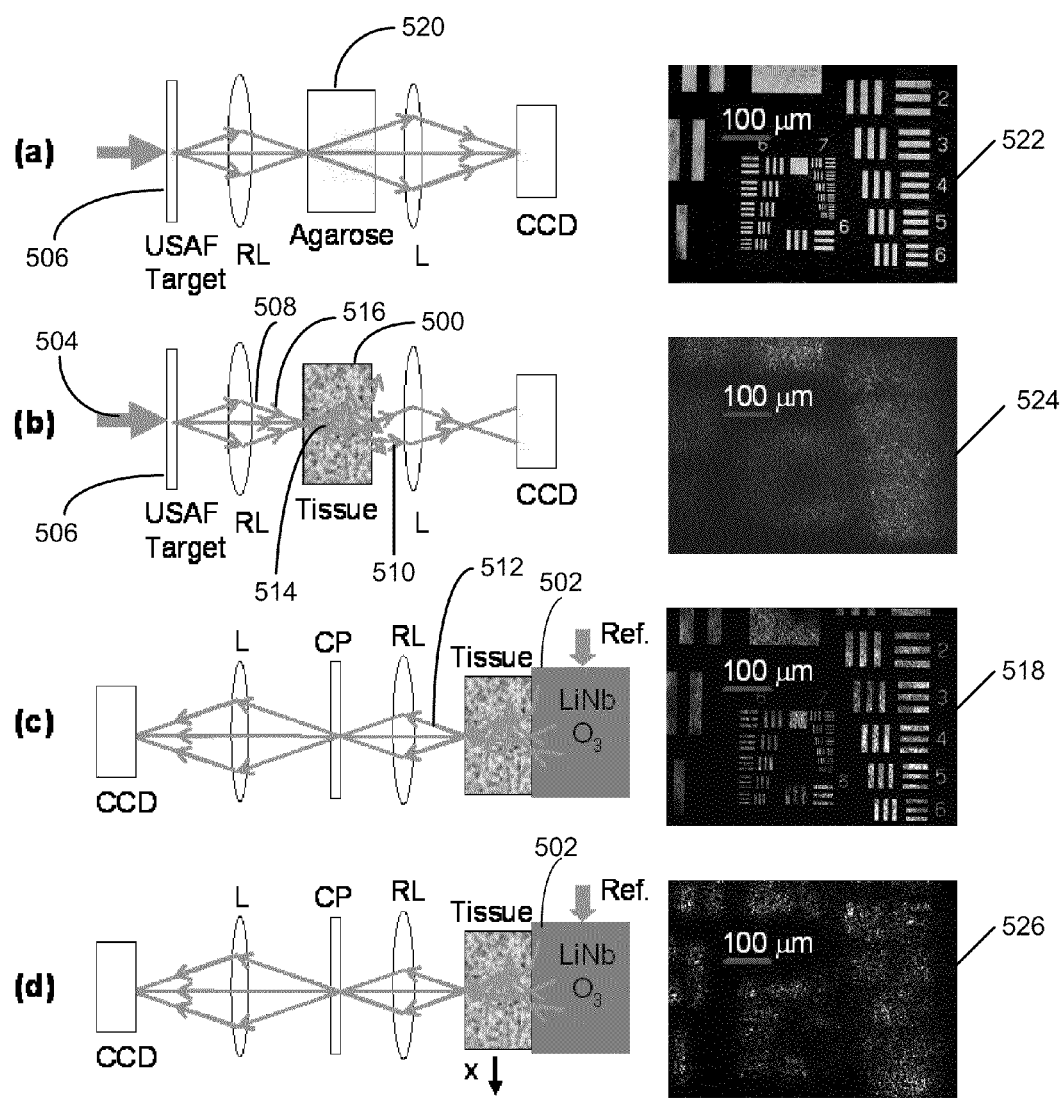
FIG. 5 (a) illustrates transmission through agarose, FIG. 5 (b) illustrates transmission through a 0.5 mm thick chicken breast tissue.

The basic features of TSOPC are illustrated in the first set of experiments (FIG. 5(*a*)-(*d*)). In this study, the scattering medium was a 0.46 mm thick chicken breast tissue section 500. A photorefractive crystal (e.g., a 45°-cut 0.075% Fe-doped Lithium Niobate) was employed as the optical recording medium 502. The light source 504 used in the experiment was a 532 nm DPSS laser. A fraction of the light is put through a United States Air Force resolution test chart (USAF) target 506 and focused 508, using a lens (RL), the pattern onto Face 1 of the tissue section 500. The scattered transmission 510 through the tissue exiting from Face 2 was then recorded onto the optical recording medium 502 with the help of the reference beam (siphoned from the same light source 504). Experimentally, ~5 mW/cm$^2$ light intensity was typically used on the USAF target 506. The present invention is not limited to the use of USAF targets. Other masks and other objects or images may be used.

To generate OPC light 512 comprising a copy of the light field of the transmission 510, the pattern stored in the crystal 502 is read out by sending in a beam along the direction opposite to the recording reference beam. During the playback process, the USAF target 506 was removed. If TSOPC does work, one would expected to see the OPC light 512 retrace the original light trajectory 514 through the tissue 500 and return the original light field 516 of the out of Face 1. A reconstruction 518 of the original USAF pattern should occur at the location (e.g., on a charge coupled display, CCD) where the USAF target 506 was.

FIG. 5 (*a*) and FIG. 5 (*b*) show USAF target imaging through 0.46 mm thick agarose 520 and the tissue section 500, respectively, using plane wave illumination. The USAF target 506 is clearly reproduced (as evidenced by image 522 on the CCD) through the agarose 520, but not reproduced (as evidenced by the image 524 on the CCD) through the tissue section 500.

For comparison, FIG. 5 (*c*) shows the reconstructed USAF image 518 as viewed using data on the CCD through the 0.46 mm thick tissue section, using the OPC wave 512. The OPC wave is imaged on the CCD by lens L.

The tissue scattering coefficient was measured to be 38 mm$^{-1}$, at the wavelength used, in a separate experiment, by interferometrically measuring the strength of the ballistically propagating transmission component for different thin tissue sections. This result implies that, on average, a photon is scattered 17 times in a 0.46 mm thick tissue sample during a single pass. In addition, the total transmission through the sample is reduced by absorption and backscattering. In a separate transmission experiment, the sum of the reduced scattering coefficient and the absorption coefficient was measured to be 0.45 mm$^{-1}$. This implies that ~19% of the input light did not reach Face 2 during the recording process. The geometry of the crystal implies a nominal maximum range of 66°, beyond which the scattered light from the tissue 500 cannot be effectively recorded. These two factors imply that a significant fraction of scattered light field information was not recorded. However, the high quality of the reconstructed image 518 in FIG. 5(*c*) demonstrates that the conjugated signal beam or light 512 can indeed retrace its initial trajectory through the tissue 500 to a good degree, in spite of these issues, wherein a compensation glass plate (CP) is shown.

FIG. 5 (*d*) shows degradation of TSOPC transmission when the sample 500 is shifted by x, as evidenced by the degraded image 526 viewed on the CCD.

Figure 6:
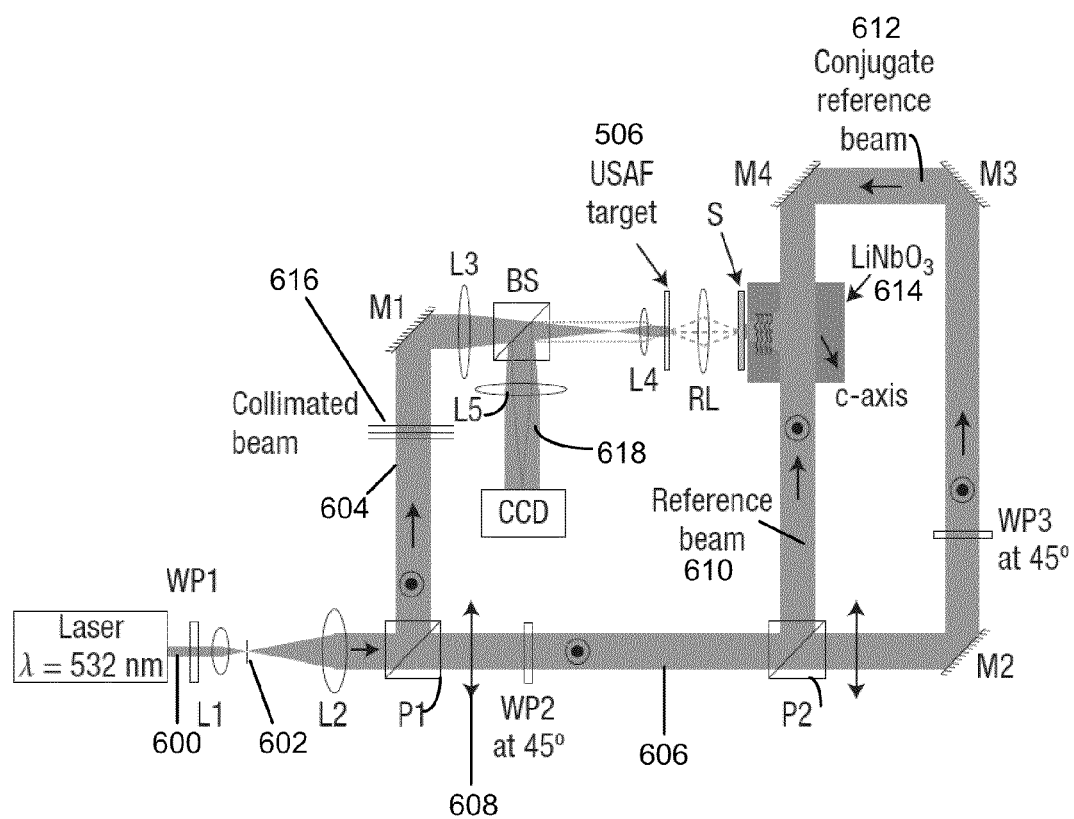
FIG. 6 illustrates an experimental set-up to confirm the TSOPC phenomenon in biological tissues, wherein the concentric (black) dots and circles represent vertical polarization, and the double-ended arrow in the plane of the paper symbolizes horizontal polarization.

The experimental scheme of the TSOPC setup used in FIG. 5(*a*)-(*d*) is shown in FIG. 6.

FIG. 6 illustrates a laser outputting a beam 600 of light having a wavelength λ=532 nm, the beam passing through a first waveplate (WP1), a first lens L1 and a pinhole 602 for spatial filtering, and a lens L2 for collimating the beam. The collimated beam is split into two beams 604, 606 by first polarizing beam splitter P1, wherein the beam 604 is polarized in a direction into the plane of the paper (as indicated by the dot surrounded by a circle) and the beam 606 is polarized in the plane of the paper (as indicated by the double headed arrow 608). Beam 606 passes through a second waveplate WP2 at 45° to rotate the polarization into the plane of the paper, and beam 606 is split into a reference beam 610 and a conjugate reference beam 612. The reference beam 610 and conjugate reference beam 612 are alternately blocked and unblocked based on whether the present invention is writing on or reading out the crystal (LiNbO$_3$) 614. Also shown are a third waveplate WP3 and second polarizing beam splitter P2.

The collimated beam 604 is directed to the sample S via mirror M1, lens L3, beamsplitter BS, lens L4, USAF target 506, and relay lens RL. The conjugate reference beam 612 is directed to the crystal 614 via mirrors M2, M3, and M4. The collimated beam 604 comprises plane wavefronts 616. The OPC beam 618 produced is directed to the CCD via BS and lens L5.

In this set of experiments, OPC is used to reconstruct a full image (USAF target) 506, which comprises of a large number of optical modes (>10$^4$). For OPC-4Pi microscopy, one only needs to reconstruct the focus of one lens, a single optical mode, which is experimentally easier to implement.

To test the thickness limit of reconstructing a single optical mode through tissue sections S, lenses L3, L4, the relay lens RL, and the USAF target 506 were removed in FIG. 6 (using a plane wave as input) and chicken tissue sections 3, 6 and 10 mm thick were used as the scattering medium S. The OPC reconstructed signal strength decreases as the sample thickness increases since the transmission efficiency is lower in thicker samples. The quality of the reconstructed spot, defined as the ratio of the original spot size vs. OPC reconstructed spot size, is rather consistent as shown in FIG. 7(*a*)-(*d*).

Figure 7:
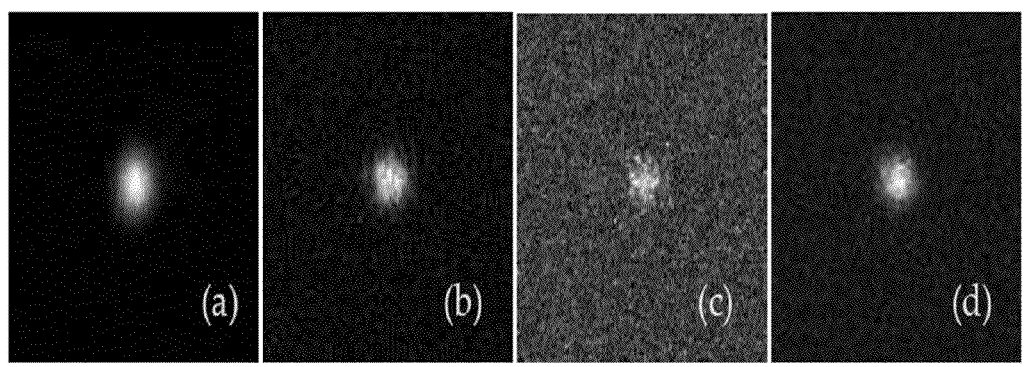
FIG. 7 illustrates OPC images reconstructed through 3 mm (FIG. 7(a)), 6 mm (FIG. 7(b)), and 10 mm FIG. 7(c, d) thick chicken breast tissues, wherein 2 mW input power is used to acquire FIG. 7(a) and FIG. 7(b), 10 mW and 50 mW input power are used in FIG. 7(c) and FIG. 7(d) respectively.

FIG. 7 illustrates OPC images reconstructed through 3 mm (FIG. 7(*a*)), 6 mm (FIG. 7(*b*)), and 10 mm FIG. 7(*c*, *d*) thick chicken breast tissues, wherein 2 mW input power is used to acquire FIG. 7(*a*) and FIG. 7(*b*), 10 mW and 50 mW input power are used in FIG. 7(*c*) and FIG. 7(*d*) respectively.

The sample thickness is limited to 100-200 μm in 4Pi microscopy by the working distance of the high NA oil or water immersion objective lenses. Based on the experimental results shown in FIG. 7(*a*)-(*d*), embodiments of the present invention may compensate the aberration and generate a high quality focus through 10 mm thick chicken tissue sections, showing an aberration compensation capability that is more than adequate for a 4Pi system.

TSOPC in Living Tissues

One application of the OPC-4Pi system is to image complex living cells and embryos. However, is TSOPC stable in living tissues? How fast does the living tissue perturb the light scattering? To answer these questions, embodiments of the present invention performed TSOPC experiments through a live rabbit ear. The experiment setup is similar to the one shown in FIG. 6 with L3, L4, relay lens, and the USAF target removed. The scattering medium in this study is a shaved ear (~1 mm thick) of a New Zealand rabbit. To separate the different mechanisms which can perturb tissue scattering, the present invention performed TSOPC experiments when the rabbit was alive, and 0.5, 1, 2, 3, 24 hours after the rabbit was euthanized. Five seconds recording time was used throughout the experiments.

Figure 8:
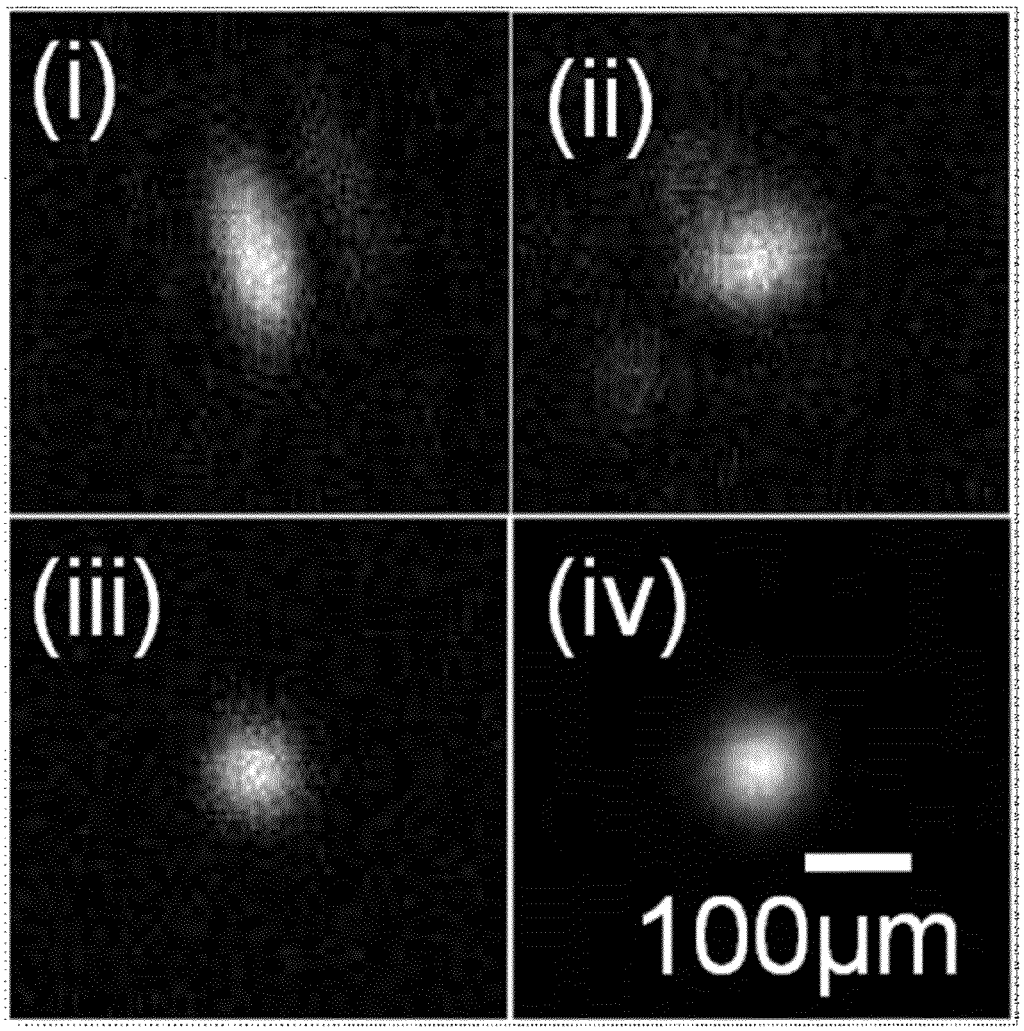
FIG. 8 illustrates reconstructed TSOPC images through the ear of a rabbit when it is alive (FIG. 8(i, ii)) and 30 minutes after euthanasia (FIG. 8(iii)), and through a tissue phantom of comparable scattering property FIG. 8(iv)

FIG. 8(*i*)-(*iv*) show the reconstructed TSOPC images through the ear of a rabbit when it was alive, as shown in FIG. 8(*i*),(*ii*), 30 minutes after euthanasia (FIG. 8(*iii*)) and through a tissue phantom of comparable scattering property FIG. 8(*iv*). The images reconstructed through the ear of the euthanized rabbit FIG. 8(*iii*) and the tissue phantom FIG. 8(*iv*) were similar round spots ~68 micrometers in diameter, as expected from the 1.5 mm input beam diameter and the 150 mm lens in front of the camera. The images reconstructed through the live rabbit's ear however deviated from the expected round spot, as shown in FIG. 8(*i*),(*i*), indicating that the scattering structures in the tissue varied during the recording process (5 seconds recording time).

Several mechanisms can perturb the tissue scattering. First, the heart beat causes tissue vibration and bulk motion, which can move the tissue to a much greater length scale than the optical wavelength. Second, the cells are functioning in live tissues undergoing active processes, and they vary their shape, size, and location over time. Third, living tissues are semi-fluidic media. The Brownian motion of the particles in tissues can alter the tissue scattering in time. All of these factors can significantly perturb the TSOPC signal, and each of them has its own time scale.

Figure 9:
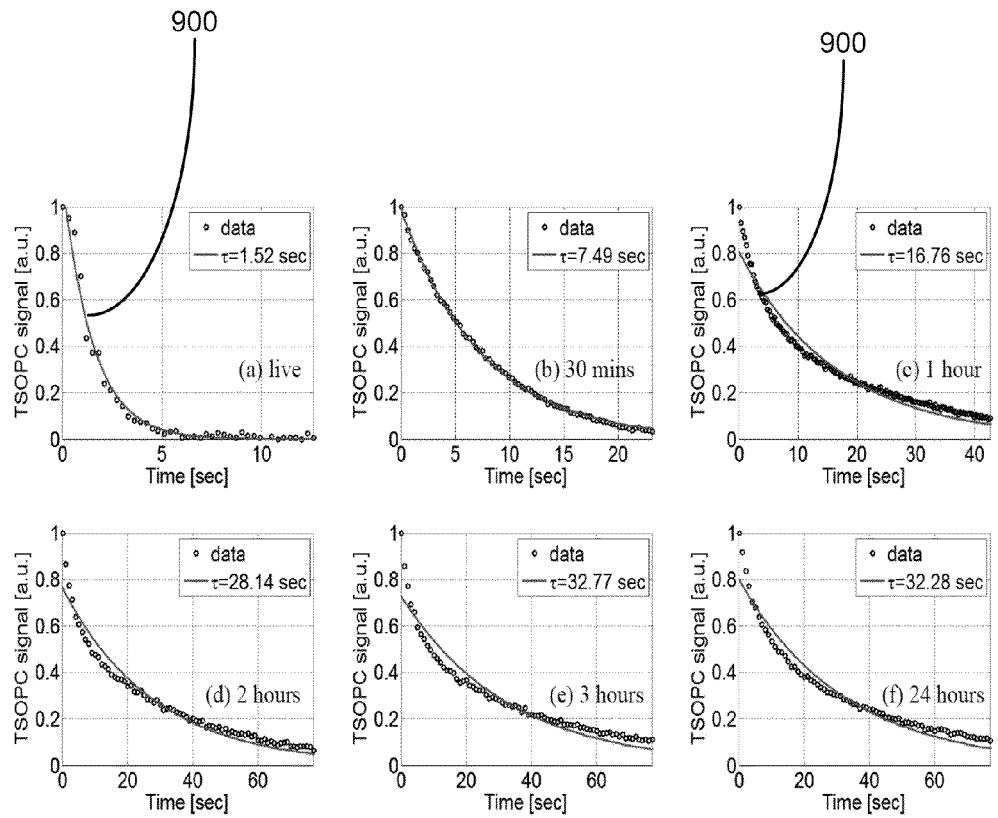
FIG. 9 (a-f) illustrate TSOPC signal decays measured when the rabbit is alive and 0.5, 1, 2, 3, 24 hours after the ear is excised, wherein the data is fitted with an exponential function.

FIG. 9 (*a*)-(*f*) show the TSOPC signal decay curve measured when the rabbit was alive, as well as 0.5, 1, 2, 3, and 24 hours after the ear was excised. An exponential function a·exp(−t/τ) was used to fit 900 the decay and yield the decay constant τ. As predicted from FIG. 8 (*i*), (*i*), the perturbation in the live rabbit ear (FIG. 9 (*a*) τ=1.5 sec) was indeed faster than the OPC recording time (5 sec). After the excision, the decay time quickly increased and then gradually reached a plateau (τ=0.5 min). The initial decay time variation can be attributed to the heart beat that stops affecting tissue scattering after excision. At that time, the cells in tissues are initially alive and gradually stop their functioning. In ~2 hours, the decay rate reaches a plateau that is still much faster than the decay rate of the tissue phantom (τ=2 min). This effect may be associated to the fluidic environment inside the tissues and the associated Brownian motion.

In some applications of the OPC-4Pi system, complex cells and embryos may be studied. In these applications, heart beat is no longer an issue. Based on this study, the rate at which live cells can perturb light scattering is below 1 Hz, slow compared to the response time of the DOPC system (1 KHz).

Digital Optical Phase Conjugation (DOPC)

The technology of OPC was originally developed in the field of nonlinear optics. The generation of phase conjugation field has traditionally relied on various nonlinear effects, such as photorefractive effect based on second order nonlinearity, optical Kerr effect and stimulated Brillouin scattering based on third order nonlinearity. Generally, the application of these nonlinear effects requires special laser systems and nonlinear crystals.

It is ideal to have a system which can work with a broad range of light sources, especially weak and long wavelength light for biomedical applications, and require no nonlinear crystals. Embodiments of the present invention provide a system with such capabilities. Two separate steps may be used to generate phase conjugate fields. In step 1, digital holography is used to measure the input optical field both in amplitude and in phase. In step 2, a spatial light modulator (SLM) is used to output the phase conjugate of the input. The experimentally challenging part is how to map the measured phase and amplitude profile to the SLM output. A calibration procedure may be used to accurately perform the mapping and experimentally test the accuracy of the system.

Figure 10:
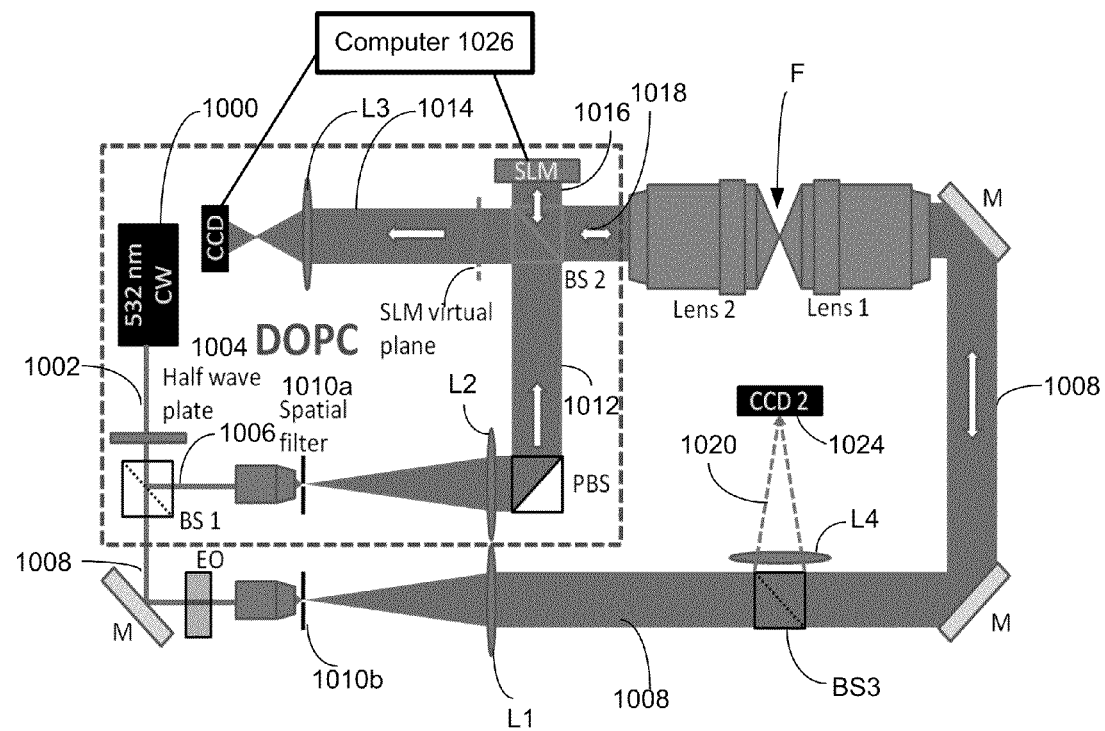
FIG. 10 illustrates an experimental scheme for testing the DOPC system, wherein BS, beam splitter, M, mirror, PBS, polarization beam splitter, EO, phase modulator are shown, and the elements of the DOPC system are enclosed in the dashed box.

FIG. 10 shows the experimental scheme of embodiments of the present invention used to test the DOPC system. The elements of the DOPC are enclosed in the dashed box in FIG. 10. A low power continuous wave (CW) green laser (532 nm) 1000 is used as the light source in this experiment. The laser output 1002 is polarization controlled by a half-wave plate 1004 and split to two beams 1006, 1008 by a beam splitter (BS 1), one beam 1006 for the DOPC system and the other beam as a test beam 1008. The information relevant for generating phase conjugate is the spatial phase profile.

To ensure a background free wavefront measurement, the light 1006, 1008 is sent through a spatial filter 1010a, 1010b (a lens and a pinhole) to clean up its spatial mode. The spatially filtered output 1012 is split into two beams 1014, 1016 by a beam splitter (BS 2), one used as a reference beam 1014 for digital holography measurement, and the other used as the input beam 1016 to the SLM. The SLM employed in this experiment is based on a reflective LCOS display such that the light reflected by the SLM is modulated. Thus, the beam splitter (BS 2) in front of the SLM plays three roles. First, it splits the spatially filtered beam 1012 into the reference beam 1014 and the input 1016 of the SLM. Second, it directs the output beam 1018 of the SLM to the target, an objective lens (lens 1 and/or lens 2) in the case of DOPC-4Pi. Third, it transmits the light 1008 counterpropagating with respect to the SLM output 1018 and combines it with the reference beam 1014 for the digital holography measurement.

The light 1008 is spatially filtered using spatial filter 1010b, collimated using lens L1, and guided to the lens 1 and lens 2 objectives using mirrors M. Lens L2 collimates the beam 1012 and lens L3 focuses the reference beam and the light 1008 on the CCD.

The digital holography employed in this experiment is based on phase shifting interferometry. The idea is to modulate the relative phase between the unknown optical wave front of beam 1008 and the reference wave 1014 and measure the corresponding interference pattern. Suppose the unknown wave front of beam 1008 is $E(\vec{r})\exp(i\phi(\vec{r}))$ and the reference wave 1014 is $E_{ref}$. The interference pattern of the two waves can be written as $E(\vec{r})^2+E_{ref}^2+2E_{ref}E(\vec{r})\cos(\phi(\vec{r}))$. If the relative phase between the two waves is increased by $\pi/2$, $\pi$, and $3\pi/2$, the $\cos(\phi(\vec{r}))$ in the last term in previous expression becomes $-\sin(\phi(\vec{r}))$, $-\cos(\phi(\vec{r}))$, and $\sin(\phi(\vec{r}))$. With a prior measurement of $E_{ref}$, $E(\vec{r})\exp(i\phi(\vec{r}))$ can be uniquely determined. Experimentally, embodiments of invention may use an EO phase modulator EO to modulate the phase of the unknown wavefront (test beam 1008) and measure the four different interference patterns with a CCD camera, which interference patterns are processed by a computer and passed to the SLM for generating the OPC wave 1018 that is the optical phase conjugate of the unknown wavefront or test beam 1008.

To test the accuracy of the DOPC system, two opposing objective lenses (lens 1 and lens 2) of NA 0.7 may be set up. The test beam 1008 from the same laser 1000 propagates through an EO phase modulator EO and then enters one objective lens (lens 1). The transmitted light is collimated by the second lens (lens 2) and then combined with the reference beam 1014. The phase of the test beam 1008 can be modulated with the EO modulator EO and the interference pattern is measured with the CCD camera (CCD). The four interference patterns (0, $\pi/2$, $\pi$, and $3\pi/2$) can be processed by a computer and passed to the SLM. The phase conjugate wave 1018 generated by the SLM was directed to lens 2 and then collected by lens 1. Under proper DOPC operation, the output 1018 of the SLM may always counterpropagate with respect to the test beam 1008 regardless of the relative positions of the two lenses. To verify this point, a beam splitter BS3 may be set up in the path of the test beam 1008 to direct the counterpropagating beam 1018 towards a CCD detector CCD2 1024, via lens L4, which monitors both the size and the position of the DOPC signal 1020 at the focal plane of lens 1, since the CCD2 1024 and lens 1 are confocal.

Figure 11:
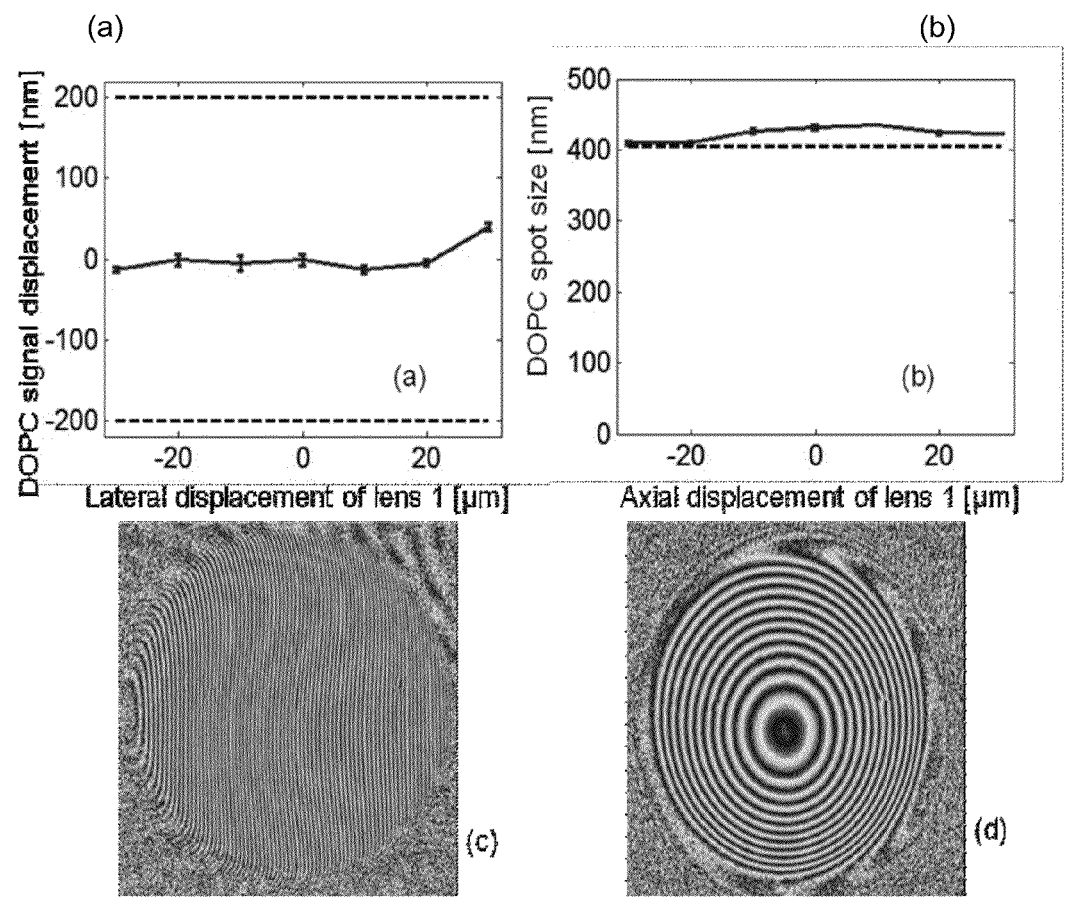
FIGS. 11 (a) and (b) are the experimental results of the lateral and axial displacement tests respectively, wherein the separation between the two dashed dark lines in FIG. 11(a) and the dashed dark line in FIG. 11 (b) represent the Full Width at Half Maximum (FWHM) of the ideal focus size, and FIG. 11 (c) and FIG. 11 (d) are the measured phase fronts when lens 1 is displaced by 30 μm in the lateral and axial direction, respectively.

In the first test, lens 1 is displaced in the lateral direction and the DOPC reconstructed spot position is monitored on CCD2 (which is the same as the focal plane of lens 1). FIG. 11 (a) shows the experimental result for lateral displacement of lens 1. As lens 1 is displaced from −30 μm to 30 μm laterally, the DOPC reconstructed signal 1018 is displaced by less than 40 nm. Two dashed dark lines are also shown in FIG. 11 (a) with their separation representing the FWHM of the ideal focus spot size or diameter (410 nm).

In the next test, lens 1 is moved in the axial direction (adjust lens separation) and the spot size or diameter variation is monitored as shown in FIG. 11 (b) with a dark dashed line representing the FWHM of the ideal focus. As lens 1 is shifted from −30 μm to 30 μm in the axial direction, the DOPC reconstructed spot size remains near diffraction limited.

FIG. 11 (c) shows the measured phase front at 30 μm lateral displacement. If the DOPC system is replaced with a mirror, the reflected focus should move from −60 μm to 60 μm.

FIG. 11(d) shows the measured wavefront when lens 1 is displaced by 30 μm in the axial direction.

The two tests show that the DOPC system can accurately perform phase conjugation to reconstruct the focus of lens 1. In FIG. 11 (c), the phase modulation is fast and there are only 8 pixels per $2\pi$ phase variation on the SLM, indicating that the phase jump per pixel is $\pi/4$. Despite the noncontinuous phase modulation of the SLM, the DOPC system can still produce accurate phase compensation with an error less than 1/1000 (40 nm/60 μm).

4Pi microscopy has stringent requirements on the alignment of the two foci. The experiment discussed here suggests that the focus alignment may be performed automatically with a DOPC system. With the assist of DOPC, the present invention can bring the two objective lenses lens 1 and lens 2 into position by checking the interference fringe pattern formed by the beam 1008 entering the 4Pi system from lens 1 and the reference beam 1014 of the DOPC system. At this point, the position of the two lenses can be fixed and the DOPC may be turned on, wherein the DOPC constantly checks the alignment and generates OPC wave 1018 to form overlapped focus. In such a way, the errors due to laser pointing instability and mechanical instability can be eliminated.

There are four advantages of choosing DOPC over conventional nonlinear optics based OPC systems. First, DOPC can work with both continuous wave (CW) and pulsed laser 1000 systems. The same DOPC can be used for both one photon fluorescence imaging with CW lasers and two-photon fluorescence imaging with pulsed lasers. Second, DOPC can work with lasers 1000 of various wavelengths, flexible for fluorescence imaging. Third, since DOPC can phase conjugate weak signals of picowatt power level or less, the DOPC is sensitive enough for phase conjugating the excitation beam 1008 in fluorescence imaging (10 microwatt–10 milliwatt). Fourth, the OPC reflectivity, defined as the power ratio between the phase conjugate signal 1018 and the input signal 1016, can be adjusted freely by computer, allowing one to ensure that the two excitation beams 1008 and 1018 at the common focus F have identical powers and hence the best excitation profile.

Combination of the DOPC with a 4Pi Confocal Fluorescence Microscope and Characterization of Its Spatial Resolution.

Figure 12:
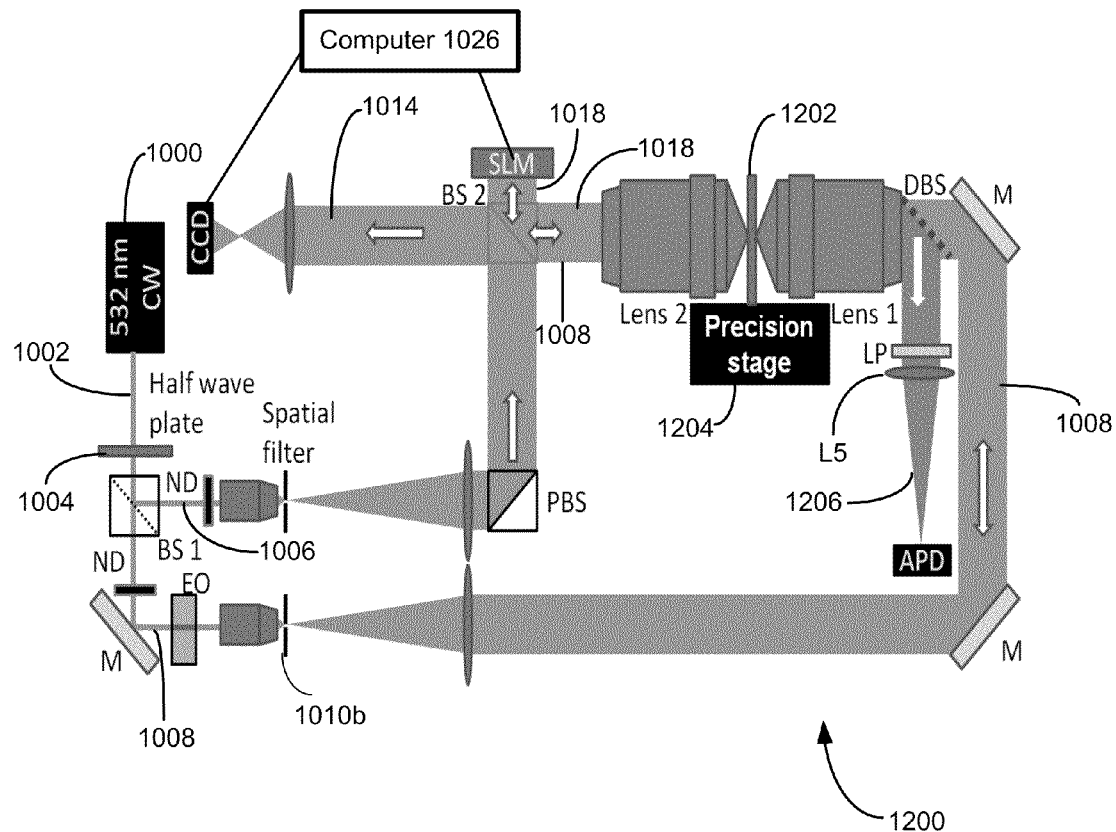
FIG. 12 illustrates an experimental scheme of the DOPC-4Pi microscope, showing ND tunable light attenuator; BS, beam splitter; M, mirror; EO, electro-optical phase modulator; PBS, polarization beam splitter; SLM, spatial light modulator; DBS, dichroic beam splitter; LP, long pass filter; and APD, avalanche photodiode.

FIG. 12 shows the experimental setup of the DOPC-4Pi microscope 1200. As discussed in previous sections, the DOPC system comprises a CCD detector (CCD) (e.g., Digital west imaging, Y Motion Pro) for measuring the interference pattern between the unknown wavefront 1008 and the reference wave 1014, and a SLM (e.g., QuantaImage) for generating the OPC wave 1018. The input 1008 to the DOPC system is a laser beam which travels through two opposing high NA oil immersed objective lenses (lens 2 and lens 1) (e.g., Nikon Apo TIRF 60× NA 1.49 oil) and the sample 1202 on a precision stage sandwiched between the two lenses. The output 1018 of the DOPC system is the phase conjugate of the input beam 1008 such that the output beam 1018 exactly retraces the input beam's 1008 way back through the two objective lenses. Although the DOPC system can work with a broad range of laser sources 1000, embodiments of the invention may use a stable lower power solid state 532 nm CW laser 1000.

The output 1002 of the laser 1000 is sent through a half wave plate 1004 for polarization control and the transmitted light is split into two beams 1006, 1008 with a beam splitter BS1. One beam 1006 is spatially filtered and this beam 1006 is sent back to the DOPC system. The other beam 1008 is sent through an EO phase modulator EO, a spatial filter 1010b and lens 1. One dichroic beam splitter DBS (e.g., Semrock Di01-R532) may be placed behind the back aperture of lens 1 to direct the fluorescence signal 1206 towards a long pass filter LP (e.g., Semrock BLP01-532R) for rejecting the laser excitation light 1008, 1018. The filtered fluorescence signal 1206 is focused by a lens L5 onto an avalanche photodiode detector APD (e.g., PerkinElmer SPCM-AQRH-14-Si) with a working area slightly smaller than the focus size for the confocal detection. The sample 1202 is securely mounted on a closed loop piezo three axis stage 1204 (PI, P-545.3R2) which performs the scanning task. The power of each excitation beam 1018, 1008 can be adjusted with a tunable light attenuator (ND) such that the foci of the two objective lenses lens 1 and lens 2 have equal power and thus the highest interference fringe contrast.

There are three ways to measure the unknown wavefront in the DOPC system. The first method is to modulate the temporal phase of the unknown wavefront of beam 1008 and record at least three interferograms, a method known as phase shifting interferometry [12] as discussed above. The advantage of this method is that the data processing is straightforward and fast. The second method requires measuring a single interferogram and the unknown phase can be retrieved with more complex mathematical algorithms. Despite a shorter measurement time (single shot), the overall time required to determine the unknown phase is longer than the first method. The third method is to add specially designed structure to the front of the CCD detector and convert the CCD detector to a wavefront sensor [13]. The data processing procedure is simple and comparable to the first method and it requires only a single measurement. Embodiments of the present invention provide such a technique, and apply such wavefront sensors to a DOPC system.

In one or more embodiments, the first method is employed, which can be easily constructed with an EO phase modulator, a CCD or CMOS camera, and a SLM, all commercially available.

The imaging speed of the DOPC-4Pi system is determined by three devices: CCD, SLM, and the sample stage 1204. The CCD detector and the SLM can run at 4 KHz and 1 KHz rate respectively, allowing an update rate of 1 KHz for the DOPC system. The sample stage is capable of fast scanning (>40 lines/sec, 30 microns/line). If the optical aberration varies slowly between adjacent data points (200 nm lateral step size, 120 nm axial step size), the scanning rate can be above 1 KHz since the aberration compensation phase profile does not need to be updated from point to point. If the optical aberration varies quickly from point to point such that DOPC needs to be performed for every data point, the imaging speed may be limited to 1 KHz. For an image of 100×100 pixels, the data acquisition time is 10 seconds (100×100/1000). Such a speed is sufficient for imaging embryos in developmental biology.

To accurately calibrate the spatial resolution of the DOPC-4Pi system, one method of the present invention uses isolated quantum dots (e.g., Invitrogen, Qdot 655 ITK), nanometer scaled robust fluorophores, as the sample to map out the axial and lateral response of the system.

In a first step, the sample is prepared. To prepare isolated quantum dots sample, diluted quantum dot solution in decane (0.001 µMol) may be spin coated on a clean No. 0 cover glass. After the solvent is evaporated, one microlitter low autofluorescence immersion oil (e.g., Olympus IMMOIL-F30CC) may be added to the spin coated surface of the cover glass, and the resultant surface may be covered with a second cover glass.

Next, the sample is first scanned in lateral directions to find a fluorescence signal from the quantum dots. Then, the axial position of the stage may be gradually adjusted during lateral scanning until the signal is maximized. The sample may be scanned over a 2 µm×2 µm×2 µm volume, from which the present invention may accurately determine the spatial resolution of the DOPC-4Pi system.

Automatic Focus Alignment

Precise alignment of the two objective lenses lens 1 and lens 2 and maintaining the PSF of the overlapped foci are crucially important to 4Pi microscopy. In conventional 4Pi microscopy, one objective lens is fixed and the other is mounted on a piezo stage. The foci of the two objective lenses are manually aligned and a position sensor is used to monitor the laser beam travelling though both lenses and the variation is compensated by shifting the lens mounted on the piezo stage.

In DOPC-4Pi system, the positions of both objective lenses lens 1 and lens 2 can be fixed after a coarse alignment. The wavefront measurement and the phase conjugation capability can ensure that the beam entering one objective lens can exactly match the beam entering the other objective lens such that the foci are always automatically overlapped.

Figure 13:
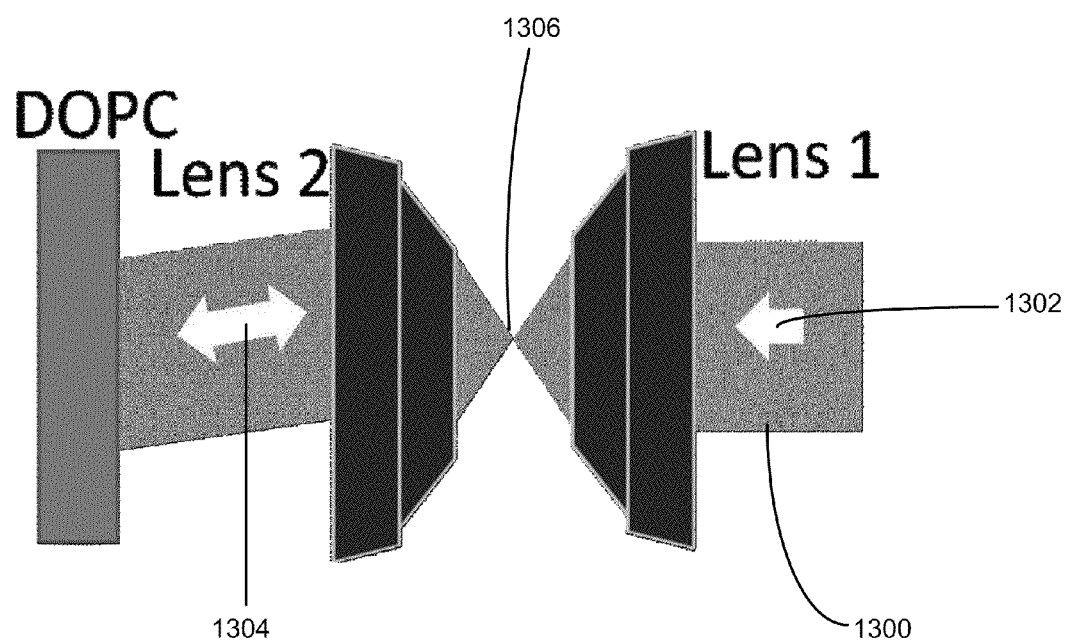
FIG. 13 illustrates automatic focus alignment.

The idea is illustrated in FIG. 13. The imperfect alignment of the objectives can cause a collimated beam 1300 which travels through both objectives lens 1 and lens 2 to deviate from the input direction 1302 and the beam may also diverge or converge. The DOPC ensures that the phase conjugate beam 1304 can always retrace the way back in a time reversed fashion and accurately focuses 1306 onto the same spot as the input beam 1300.

To experimentally verify this point, one may use isolated quantum dots as the sample and perform scanning over a 2 μm×2 μm×2 μm volume. Thus, in one embodiment, the method of checking automatic alignment comprises the following steps.

In a first step, deliberately shifting lens 2 in FIG. 12 in both lateral and axial directions.

In a second step, inserting a beam block between lens 2 and the DOPC system, to observe the spatial resolution, e.g., a resolution of 200 nm in the lateral direction and 600 nm in the axial direction (single lens confocal).

In a third step, removing the beam block and observing lateral and axial resolution. If the DOPC beam enters the 4Pi system accurately, no variation in the lateral resolution and interference fringes in the axial direction should be observed (see FIG. 1). A decrease in the lateral resolution or less than 100% fringe contrast for equal input powers in the axial direction indicates imperfect focus alignment.

One may also estimate the amount of lateral shift that can be compensated by the DOPC system. For example, if the SLM (e.g., QuantaImage) used in FIG. 10 is employed, there are 768 SLM pixels in each dimension for phase modulation. Eight pixels can be used to accommodate the phase variation of 2Pi such that the phase difference between adjacent pixels is Pi/4, and the total phase variation across the 768 pixels is 192Pi (96λ), where λ is the laser wavelength. If the entire 768×768 pixels are imaged onto the back aperture of the objective lens 1, wherein back aperture is ~6 mm in diameter, the maximum deviation angle that can be compensated is 96λ/6 mm and the maximum deviation at the focal plane is 96λf/6 mm, where f is the focal length of the objective lens 1. As an example, for an Olympus 60× objective, f is ~3 mm and the maximum deviation is therefore ~26 microns, such that the present can use the SLM to automatically compensate the relative displacement between the two objectives over a ~50× 50 micron area.

The phase modulation caused by axial displacement of the objectives is slower (depending on the NA of the objective) as shown in FIG. 11 (d). Consequently the axial compensation range is greater than 50 microns for a 60× objective. Experimentally, the displacement of the objectives caused by mechanical instability is much smaller than one micron, such that the available compensation volume is more than enough.

Aberration Compensation Capability of the DOPC-4Pi Microscope and Quantitative Determination of the Compensation Limit with Tissue Phantoms.

Figure 14:
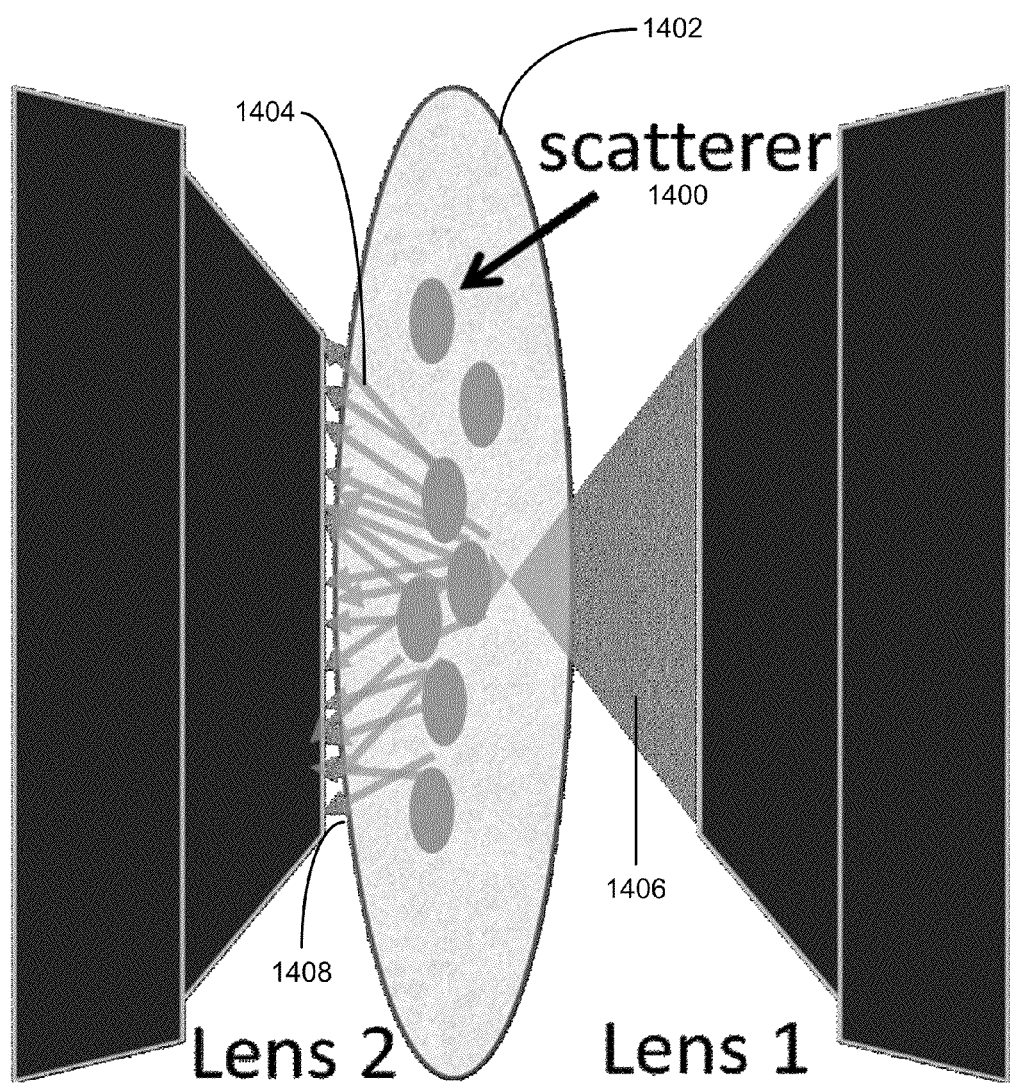
FIG. 14 illustrates compensation of aberration with the DOPC-4Pi system.

The key advantage of using DOPC-4Pi system over a conventional 4Pi system is that the DOPC-4Pi system can compensate optical aberrations. FIG. 14 illustrates the scenario where the scatterers 1400 in the middle of the sample 1402 cause focus aberration 1404 for the beam 1406 entering the sample 1402 from lens 1. If the beam 1406 from lens 1 is allowed to propagate through the scatterers and lens 2, and a DOPC system is used to generate the phase conjugate of the transmitted light 1408, the focus aberration can be completely healed. In such a way, the embodiments of the invention can perform high resolution imaging (200 nm lateral, 120 nm axial) on both sides of the scattering medium 1402.

Before applying such techniques to biological samples, the quality of the phase conjugate focus and the turbidity compensation limit should be measured. One embodiment of the measurement of the present invention's system comprises the following steps, for example, using polystyrene microspheres as the scatterers.

In a first step, diluted quantum dot solution in decane (0.001 μMol) is spin coated on a clean No. 0 cover glass and the decane solvent is allowed to evaporate. In a second step, adding monodispersed polystyrene (n=1.60 at 532 nm) beads one micron in diameter (Polysciences) in water to the spin coated surface of the cover glass placed on a heater plate of 80° C., which speeds up the water evaporation. During the evaporation, the polystyrene beads may form a multilayered sheet whose thickness may be controlled by the amount of polystyrene beads added during evaporation.

In a third step, adding one drop (one microliter) of low auto-fluorescence immersion oil (e.g., Olympus IMMOIL-F30CC, n=1.52 at 532 nm) to the surface of the polystyrene beads and sandwiching the oil drop between the polystyrene cover glass and the quantum dot cover glass. In such a way, the sample has isolated nanometer scaled fluorophores on one side and a scattering medium on the other side.

The property of the scattering medium can be adjusted by using polystyrene beads of different diameter (0.1 micron-15 microns) and varying the thickness of the scattering medium from 20 to 200 microns.

In a fourth step, images with high axial resolution are acquired through the scattering medium, using the DOPC-4Pi system. For each prepared sample, isolated quantum dots are found and scanned over a 2 μm×2 μm×2 μm volume, which indicates the size and shape of the overlapped foci. Moving the quantum dot around the laser focus while measuring the excited fluorescence signal and looking at the signal change may map out the point spread function of the imaging system, which tells if the present invention has a nice sharp focus. Based on OPC reconstruction quality, one can expect consistent image quality in samples of different thickness and scattering properties.

Two Photon DOPC-4Pi Microscopy

One or more embodiments of the invention may employ a femtosecond laser (e.g., 80 fs pulses) to demonstrate two-photon DOPC-4Pi microscopy.

Although the DOPC-4Pi system can accurately compensate optical aberration and produce well overlapped foci, the generated fluorescence signal is at a different wavelength and its propagation out of the sample is still affected by scattering. The distorted fluorescence wavefront can cause severe trouble for confocal imaging which relies on rejecting out of focus signal with a pinhole. With a distorted wavefront, the fluorescence signal can no longer be properly focused through the pinhole.

Such a problem can be solved nicely with two-photon excitation which can produce a three dimensionally confined excitation volume. The spatial resolution is solely determined by the excitation point spread function and the entire generated fluorescence signal is originated from the focus. A large area detector should be used to collect the scattered fluorescence light. Another benefit of two-photon excitation is that the excitation light is at longer wavelength and the light scattering is inherently much less than using shorter wavelength light. In addition, the center peak in the axial intensity distribution shown in FIG. 1(c) becomes more pronounced, and the side peaks will be suppressed since the signal is proportional to the intensity square.

Embodiments of the invention provide a method to combine the advantages of two-photon microscopy with DOPC- 4Pi to improve the axial resolution of conventional two-photon microscopy by a factor of 5 to ~140 nm. A few adjustments need to be made in order to adapt the DOPC-4Pi system for two-photon excitation.

First, the path of the reference beam needs to be separated from the SLM input beam. Separated time delay controls can be used to ensure the two 80 fs pulses meet at the objective lens foci and the reference beam (80 fs) may also time-overlap and interfere with the beam traveling through the 4Pi system.

Second, the pinhole in front of the detector is replaced and the detector needs to have a large active area to collect the scattered fluorescent signal.

Third, spectral dispersion needs to be minimized and compensated to provide transform limited pulses at the objective lens foci.

Figure 15:
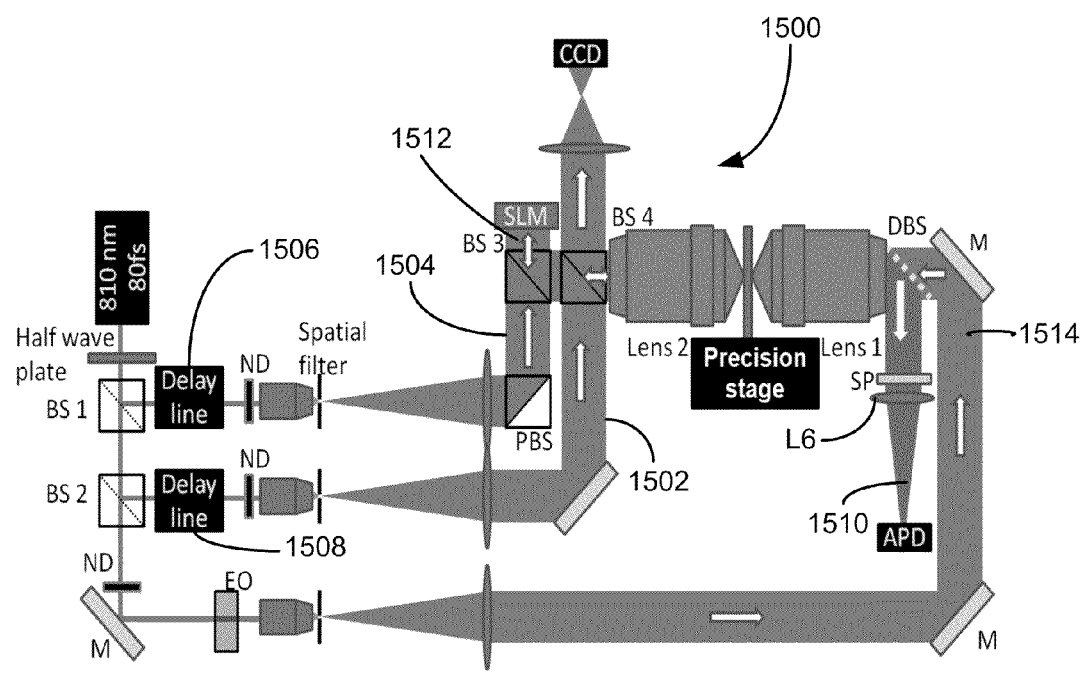
FIG. 15 illustrates an experimental setup of the two-photon DOPC-4Pi microscope, wherein BS, beam splitter; ND, tunable light attenuator; M, mirror; EO, electro-optical phase modulator; PBS, polarization beam splitter; SLM, spatial light modulator; DBS, dichroic beam splitter; SP, short pass filter; APD, and avalanche photodiode are shown.

FIG. 15 shows the experimental setup of the two-photon 4Pi system 1500. The main difference between FIG. 15 and FIG. 12 (one photon confocal) is that the reference beam 1502 in FIG. 15 is separated from the SLM input beam 1504, using beamsplitters BS1, BS2, and time delay controls 1506, 1508 are applied to both the SLM input beam 1504 and the reference beam 1502. In addition, the detector APD has a larger active area and the lens L6 in front of the detector APD has much shorter focal length such that the focus size is much smaller than the active area of the detector APD. In such a way, the scattered fluorescence signals 1510 propagating towards different directions can be collected. The pulse dispersion compensation elements are not shown in FIG. 15 for simplicity. Also shown is beamsplitter BS4.

To match the timing of the SLM output 1512 and the beam 1514 entering from lens 1, embodiments of the invention may again use isolated quantum dots as the sample. The quantum dot may first be brought to the overlapped foci of the two objective lenses lens 1 and lens 2, and then the time delay 1506 may be adjusted on the SLM output 1512 until the signal 1510 starts to oscillate due to the interference between the two 80 fs pulses 1512, 1514. This alignment requires only moderate accuracy since the pulse duration (80 fs) corresponds to 24 microns length in free space, much longer than the axial distribution of the focus (~700 nm). To calibrate the two-photon DOPC-4Pi system, the procedure may be repeated to determine the spatial resolution and the measurements may be repeated to measure the focus quality during aberration compensation. At the end of these measurements, the two photon DOPC-4Pi system may be used for imaging biological samples.

Exemplary Application: Imaging *Drosophila* Embryo

Embodiments of the invention may apply two-photon DOPC-4Pi to *drosophila* embryo and demonstrate improved axial resolution.

*Drosophila* embryo is an important model in developmental biology. The yolk in the middle of the embryo is a highly scattering medium, preventing the application of 4Pi microscopy. For improving the penetration depth, two-photon microscopy is often employed for four dimensional live imaging. The achievable axial resolution is ~700 nm. One may apply the two-photon DOPC-4Pi microscopy to image *Drosophila* embryo with a significantly improved resolution of 140 nm.

For in vivo imaging, the embryo needs to be kept in water, and sandwiching the sample between cover glasses should be avoided since it can deform the embryo and prevent its normal development. To meet these requirements, a water immersion lens (suitable for samples in water) may be used, and one side of the embryo may be attached onto a cover glass coated with glue [14], leaving the other side open to water. To improve the penetration depth and the fluorescence signal collection efficiency, a water immersion objective with a large NA, a long working distance, and a low magnification (e.g., Carl Zeiss C-Apochromat, 40×, NA 1.1, 0.6 mm working distance) may be used. The low magnification is especially useful for collecting the multiply-scattered fluorescence signal.

For the initial demonstration, the nuclear fluorescent labeling (GFP) may be used, since the spatial position of the nucleus can indicate the position of a cell, allowing the monitoring of the cell movement and cell division. In addition, *drosophila* embryos expressing GFP are available from Bloomington Stock center. To take advantage of the improved axial resolution, embodiments of the invention may apply the DOPC-4Pi technique to image smaller structures, such as mitochondria and cytoskeleton located at different depths within the embryo.

To efficiently excite GFP, a Ti: sapphire oscillator may be tuned to 930 nm, and the SLM spectral calibration file for 930 nm may be loaded. Another adjustment is to replace the dichroic beam splitter DPS and the short pass filter SP accordingly.

To achieve the best axial resolution improvement, embodiments of the invention may correctly overlap the foci of the two objective lenses (achieved with DOPC) and supply equal powers to both foci. To balance the excitation powers from both objective lenses, the foci may first be overlapped with the help of DOPC and then one beam may be blocked followed by measuring the strength of the fluorescence signal. The input power ratio can then be adjusted until the fluorescence signals excited by each lens (lens 1 and lens 2) individually are equal. In addition, the detected fluorescence signal from embryo tissues is known to scale as Signal(z) $\propto \exp(-2z/L)$ where L is the scattering mean free path, and the factor of 2 comes from the two-photon excitation. L can be simply measured by using one lens for excitation and measuring the fluorescence signal during a z axis scan. Knowing L, one can simply program the motorized light attenuator to ensure the excitation powers from both objectives are always equal during the z axis scan. One can expect to see a fivefold improvement in axial resolution as compared to a conventional two-photon microscope.

Advantages and Improvements

FIG. 16(a)-(e) illustrates the improved high-resolution 3D microscope and deep tissue biochemical imaging apparatus of embodiments of the present invention, as compared to other conventional microscopes.

Figure 16:
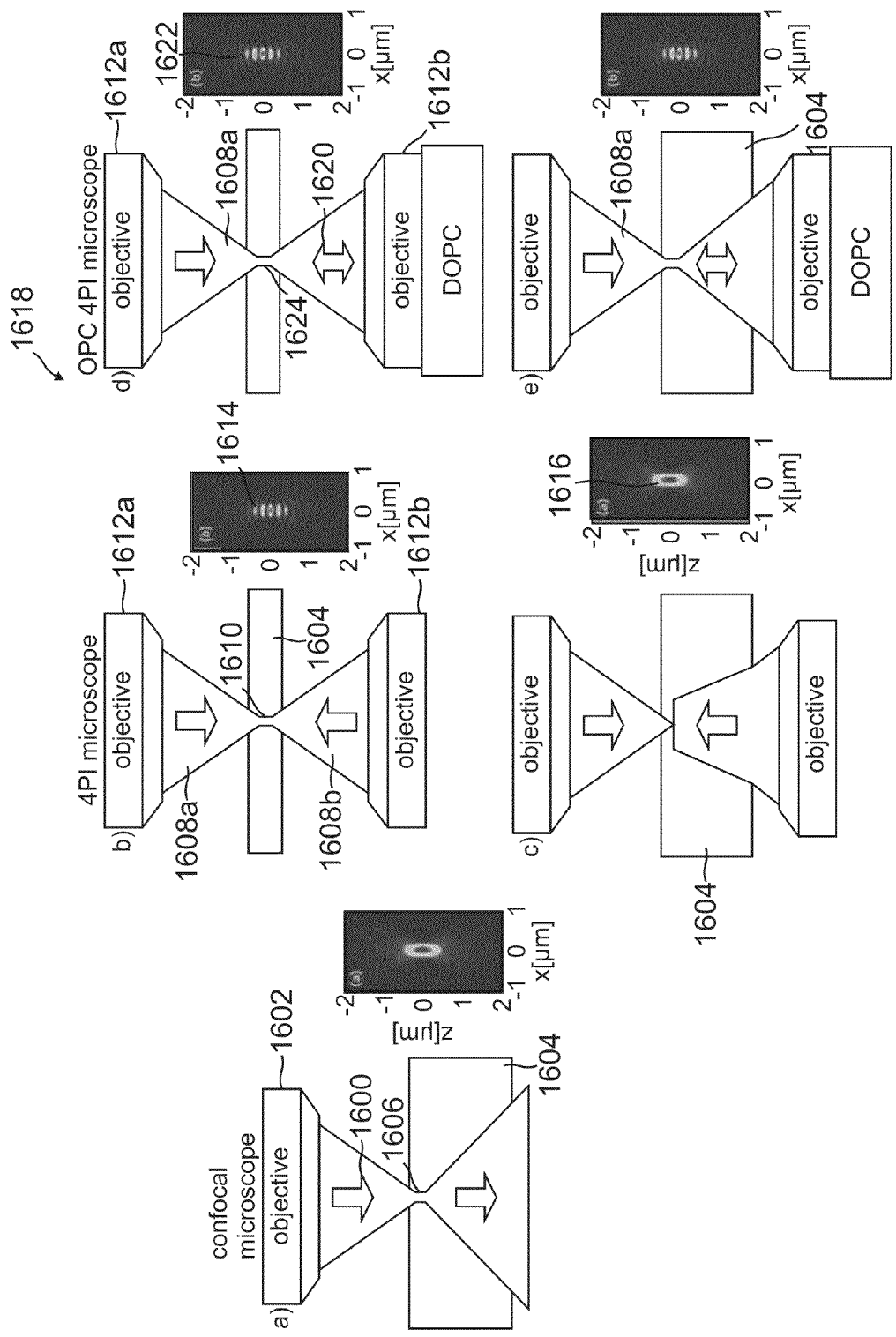
FIG. 16 (a) illustrates how a confocal microscope uses a tightly focused laser to perform high-resolution scan, wherein the axial resolution is relatively poor (~600 nm), FIG. 16 (b) illustrates how a 4Pi microscope uses 2 counter-propagating focused laser beams to generate interference axially to improve axial resolution (~120 nm), FIG. 16 (c) illustrates how a 4Pi microscope performs poorly for thick tissue sections because scattering diffuses the laser beam spots, wherein at superficial depths, the 4Pi microscope's axial resolution is comparable to a confocal microscope because one beam is too diffused to be helpful, FIG. 16 (d) illustrates how an OPC 4Pi microscope combines one of the objectives with a DOPC system, wherein the OPC field thus generated is always an exact match for the tightly focused laser beam propagating downwards, and FIG. 16 (e) illustrates an OPC 4Pi microscope may work well with thick tissue sections because the OPC field undoes the effects of scattering, wherein the penetration depth may still limited (comparable to the confocal set up) because the initial laser beam may not be able to come to a tight focus if the amount of scattering experienced by the beam is too great.

FIG. 16(a) illustrates that a confocal microscope uses a tightly focused laser beam 1600, focused using an objective 1602 to perform high-resolution scan of a sample 1604. The axial resolution is relatively poor (~600 nm), as indicated by the plot of the focus spot in FIG. 16(a) that shows the vertical and horizontal dimensions of a slice through the beam 1600 along the focal plane 1606.

FIG. 16(b) illustrates that a typical 4Pi microscope uses 2 counter-propagating focused laser beams 1608a, 1608b that are focused to the same spatial point 1610 by objectives 1612a, 1612b to generate interference 1614 axially and improve axial resolution (~120 nm), as illustrated by the plot in FIG. 16(b) as indicated by the plot of the focus spot in FIG. 16(a) that shows the vertical and horizontal dimensions of a slice through the beams at spatial point 1610.

FIG. 16(c) illustrates that the conventional 4Pi microscope performs poorly for thick tissue sections because scattering diffuses the laser beam spots 1616. At superficial depths, the 4Pi microscope's axial resolution is comparable to a confocal microscope because one beam is too diffused to be helpful.

A viable optical phase conjugation assisted 4Pi (OPC 4Pi) microscopy scheme of embodiments of the present invention is shown in FIG. 16(d). FIG. 16(d) illustrates that an OPC 4Pi microscope 1618 combines one of the objectives 1612b with a DOPC system (DOPC). The OPC field 1620 thus generated is always an exact match for the tightly focused laser beam 1608a propagating downwards, generating interference 1622 axially and improving axial resolution (~120 nm), as indicated by the plot of the focus spot in FIG. 16(d) that shows the vertical and horizontal dimensions of a slice through the beams 1620, 1608a at spatial point 1624.

FIG. 16(e) illustrates that an OPC 4Pi microscope 1618 may also work well with thick tissue sections 1604 because the OPC field will undo the effects of scattering. The penetration depth may still be limited (comparable to confocal) because the initial laser beam 1608a may not be able to come to a tight focus if the amount of scattering experienced by the beam 1608a is too great.

Thus, in the OPC 4-Pi microscope 1618, embodiments of the present invention launch a tightly focused laser beam 1608a into the sample 1604 from one side. The transmission may then be collected and measured with a DOPC system. The DOPC system is used to launch a time-reversed version 1620 of the light field back through the sample 1604. Due to the TSOPC effect, this returning beam may retrace the original transmission path and automatically come to a focus at the same location 1624 as the original beam's 1608a focus. An OPC 4Pi system 1618 may effectively self-align and thereby eliminate the primary implementation challenge of 4Pi microscopy. In addition, the ability of TSOPC to correct for scattering also means that an OPC 4Pi microscope can be used to image through thicker samples. In fact, an OPC 4Pi system should be able to image to the same depth as a confocal microscope for samples of arbitrary thickness (thickness limited only by the efficiency of the TSOPC reconstruction) (see FIG. 16(e).

Thus, the advantages of using the technique of DOPC for 4Pi microscopy are twofold.

First, 4Pi microscopy has stringent requirements on the optical alignment to ensure that the foci of the two high NA objectives are perfectly overlapped during the imaging. Experimentally, mechanical noise and instability can disrupt the perfect alignment in conventional microscopes. In addition, the heterogeneous refractive index of biological samples can also lead to misalignment. With the help of DOPC, the accurate alignment can be performed automatically and the aberration caused by the biological sample can be completely compensated, greatly reducing alignment errors.

To date, 4Pi microscopy has been limited to highly transparent samples. The second advantage of DOPC-4Pi system is that it allows the operation of 4Pi microscopy through more complex samples. As discussed earlier, OPC can be used to compensate the wavefront distortion caused by scattering through centimeter thick tissues. In the same way, embodiments of the invention may compensate for the wavefront distortion between the two objectives in 4Pi microscopy. As long as the region of interest can be accessed with one objective, DOPC can automatically form a high quality focus through the second objective. In such a way, one can greatly extend the capability of 4Pi microscopy and take advantage of the significantly improved axial resolution for imaging complex biological samples.

The advantages of using DOPC system over conventional OPC system based on nonlinear effect are: 1) the DOPC system can work with light of various wavelengths which is ideal for fluorescence imaging; 2) the same DOPC system can be used for either CW laser (one-photon fluorescence) or pulsed laser (two-photon fluorescence); and 3) the power of the phase conjugate beam can be easily adjusted by controlling the input power to the DOPC system (one may use the Ti: sapphire oscillator).

Embodiments of the invention may be used to demonstrate two-photon DOPC-4Pi microscopy and characterize its performance with tissue phantoms (e.g., using a Ti: sapphire oscillator). In addition, embodiments of the invention may apply the developed microscope to image *drosophila* with an expected fivefold improved axial resolution. The application of the DOPC-4Pi system is potentially broad. The same system can also be applied for other types of nonlinear microscopy (the phase matching condition is relaxed for sub-wavelength axial intensity distribution) such as second harmonic microscopy. One expects that the DOPC-4Pi system may be very useful in neuroscience and developmental biology in which high resolution 3D imaging can provide valuable information.

Process Steps

Figure 17:
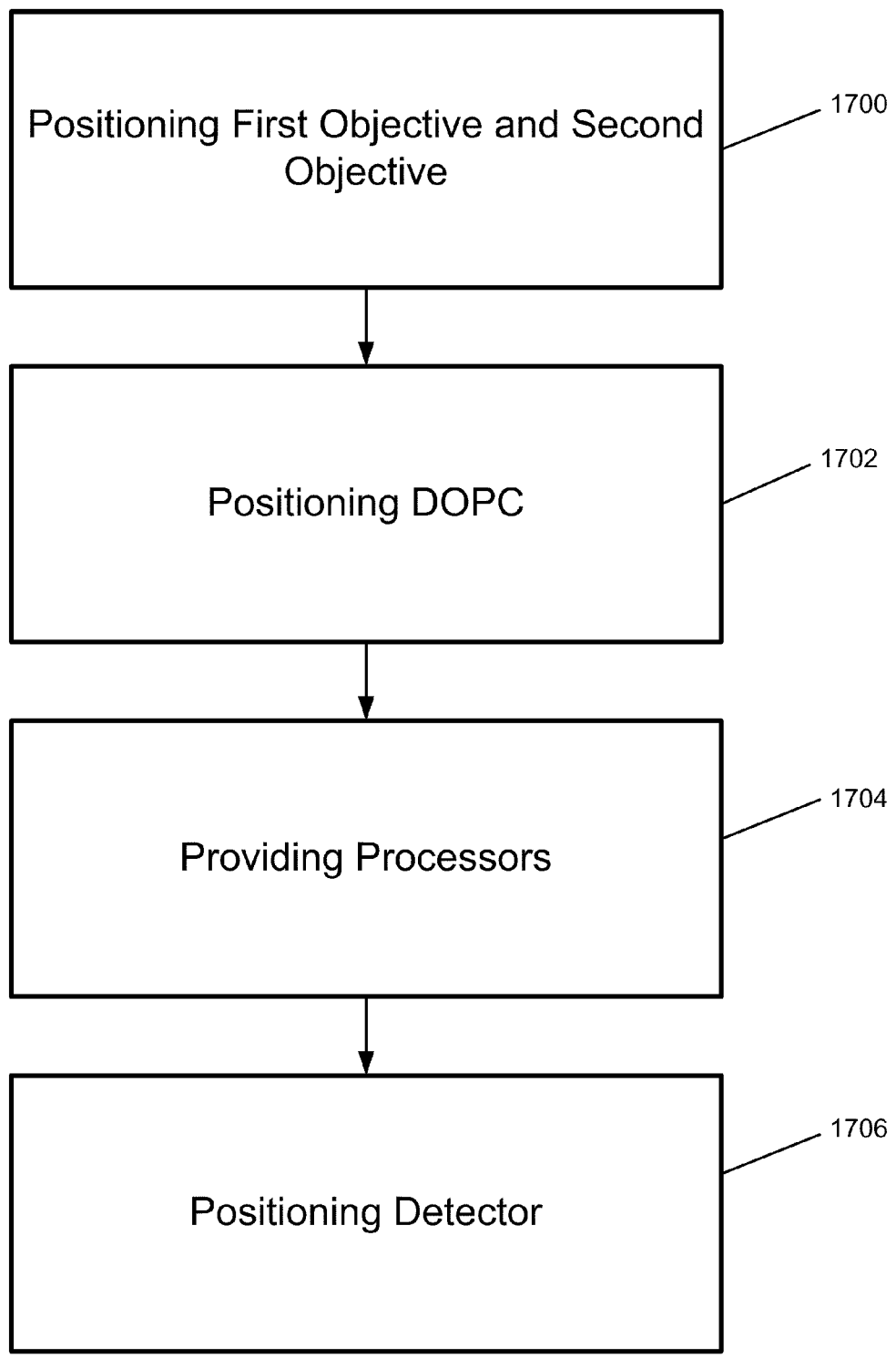
FIG. 17 is a flowchart illustrating a method of fabricating a DOPC-4-Pi microscope.

FIG. 17 is a flowchart illustrating a method for fabricating a 4-Pi microscope for imaging a sample. The method may comprise the following steps. Reference is also made to elements of FIG. 10 and FIG. 12.

Block 1700 represents positioning a 4-Pi microscope including first objective (lens 1) for focusing a first light beam 1008 on the sample 1202 at a spatial point F, and a second objective (lens 2).

Block 1702 represents positioning one or more Digital Optical Phase Conjugation (DOPC) devices, wherein the DOPC devices include (1) a sensor (e.g., CCD) for detecting the first light beam 1008 that has been transmitted through the sample 1204 and inputted on the sensor; and (2) a SLM for outputting, in response to the sensor detecting the first light beam 1008, a second light beam 1018 that is an optical phase conjugate of the first light beam 1008.

The step may further comprise positioning a second objective (lens 2) to transmit the first light beam 1008 to the sensor and focus the second light beam 1018 on the sample 1202 at the spatial point F, so that the first light beam 1008 and the second light beam 1018 are counter-propagating and both focused to the spatial point F. The step may further comprise positioning a sample holder 1204, between the first objective and the second objective, for holding the sample such that the spatial point is on or within the sample, and the first light beam is transmitted through the sample and the second objective before being collected by the DOPC devices.

The step may further comprise positioning a source 100 of an input reference beam 1016, to illuminate one or more pixels of the SLM, wherein the second light beam 1018 is a reflection of the input reference beam 1016 off the pixels of the SLM, and the pixels are for modulating the input reference beam 1016 to create the optical phase conjugate.

The step may further comprise positioning a laser 1000 that is the source for the input reference beam 1016 and a source for the first light beam 1008, wherein the first light beam 1008 and the second light beam 1018 have a wavelength such that the fluorescence is generated by two photon excitation of the sample 1202 by the first light beam 1008 and the second light beam 1018.

The DOPC devices may each have a response time or update speed of at least 1 KHz, for example. The DOPC devices can each have a response time or update speed of at least 1 KHz or faster than movements in living tissues that deteriorate Turbidity Suppression by Optical Phase Conjugation (TSOPC) reconstruction efficiency.

The step may further comprise positioning a beam splitter (e.g., BS2) to direct the first light beam 1008, and transmit a sensor reference beam 1014, to the sensor (e.g., CCD) so that the first light beam 1008 and the sensor reference beam 1014 interfere and form one or more holograms on the sensor, the holograms including interferometric data. The step may further comprise positioning an electro-optic modulator EO to control a relative phase between the first light beam 1008 and the sensor reference beam 1014, so that the holograms include one or more phase shifted holograms.

Block 1704 represents providing one or more processors (e.g., computer processors, or chips or computer 1026) for receiving the interferometric data and determining one or more phases and one or more amplitudes of first light fields of the first light beam 1008 from the interferometric data, digitally modifying the phases and the amplitudes to produce one or more modified phases and one or more modified amplitudes, and outputting the modified phases and modified amplitudes to the SLM so that the SLM outputs the second light beam 1018 having the modified phases and modified amplitudes that are the optical phase conjugates of the phases and the amplitudes.

The step may further comprise providing a computer processor or filter (e.g., ND) for controlling a power of the input reference beam 1016 so that the second light beam 1018 and the first light beam 1008 at the spatial point F have identical powers as measured by maximum phase contrast in an interference pattern formed at the spatial point F between the first light beam 1008 and the second light beam 1018, or as measured by the first light beam 1008 and the second light beam 1018 independently generating an identical fluorescence signal.

The first light beam 1008 and the second light beam 1018 may have a power at the spatial point which is sufficiently low to avoid photobleaching of the sample 1202 at the spatial point F, thereby optimizing fluorescence generated by exciting the sample 1202 at the spatial point F with the first light beam 1008 and the second light beam 1018.

Block 1706 represents positioning a detector (e.g., APD) for imaging fluorescence of the sample generated by the first light beam 1008 and the second light beam 1018.

Figure 18:
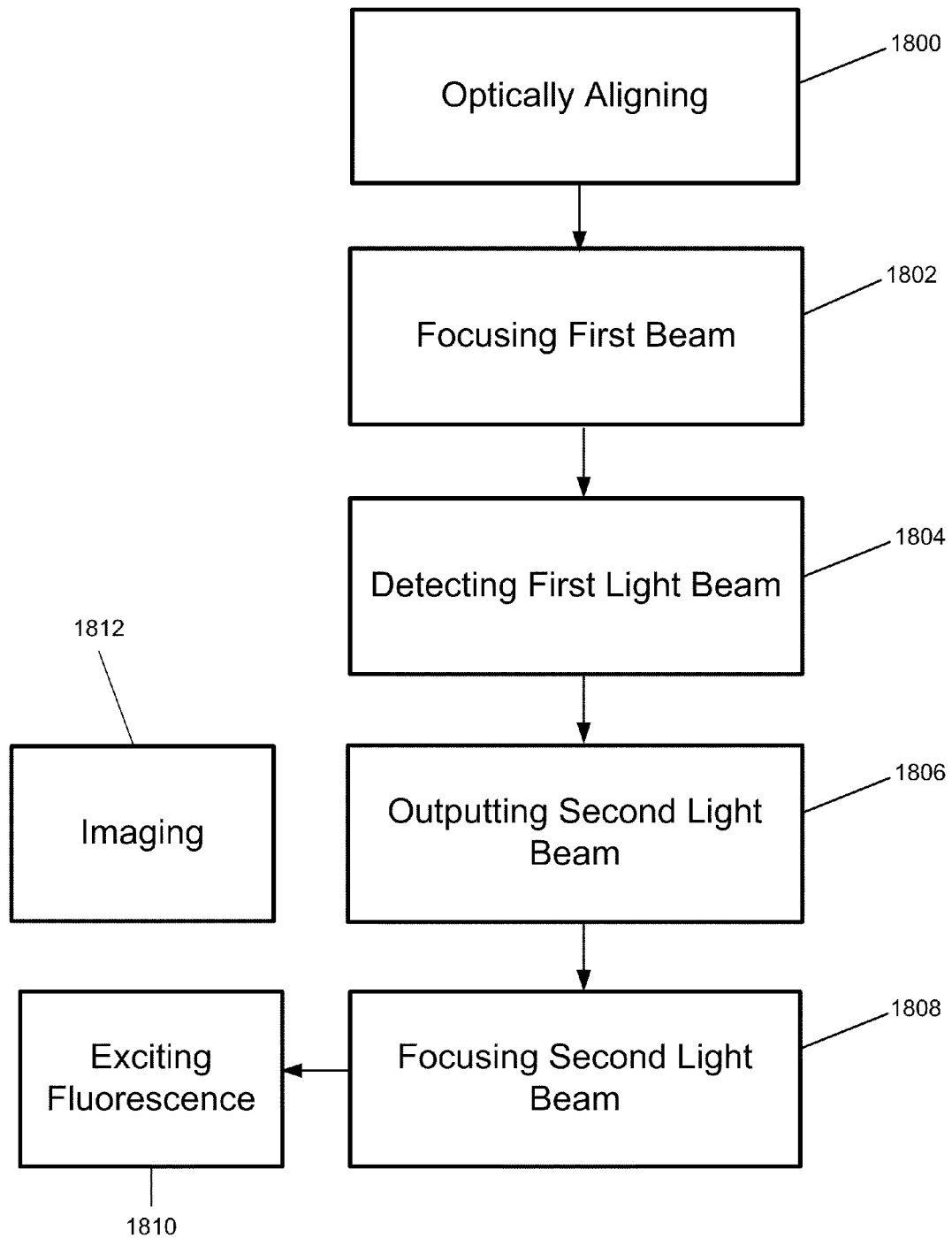
FIG. 18 is a flowchart illustrating a method of imaging a sample.

FIG. 18 is a flowchart illustrating a method for imaging a sample using a 4-Pi Microscope, using a spatial light modulator. The method may comprise the following steps.

Block 1800 represents optically aligning the objectives of the 4-Pi microscope taking advantage of OPC, according to one or more methods of the present invention. The step may further comprise measuring the aberration of the microscope (e.g., compensation limit), and the lateral, and axial resolution of the microscope.

Block 1802 represents focusing a first light beam at a spatial point on a sample.

Block 1804 represents detecting the first light beam that has been transmitted through the sample on a sensor. The step may comprise transmitting the first light beam through a second objective to a sensor. The step may comprise combining directing the first light beam to the sensor using a beamsplitter and transmitting or directing a sensor reference beam, through or using the beamsplitter, to the sensor so that the first light beam and the sensor reference beam interfere and form one or more holograms on the sensor, the holograms including interferometric data; receiving, in one or more processors, the interferometric data and determining one or more phases and one or more amplitudes of first light fields of the first light beam from the interferometric data; digitally modifying (e.g., reversing), in the one or more processors, the phases and the amplitudes to produce one or more modified (e.g., reversed) phases and one or more modified (e.g., reversed) amplitudes, and outputting, from the one or more processors, the modified phases and modified amplitudes to an SLM.

The step may further comprise controlling, using an electro-optic modulator, a relative phase between the first light beam and the sensor reference beam, so that the holograms include one or more phase shifted holograms.

Block 1806 represents outputting, using a SLM, a second light beam that is an optical phase conjugate of the first light beam, wherein the first light beam and the second light beam are counterpropagating and the second light beam retraces a path of the first light beam, thereby automatically aligning the 4-pi microscope. The SLM outputs the second light beam having the modified phases and modified amplitudes that are the optical phase conjugates of the phases and the amplitudes, e.g., as received from the processors in Block 1806. The SLM outputs the output light beam in response to the first light beam detected by the sensor and the sensor and the SLM may be included in one or more DOPC devices.

The step may comprise illuminating one or more pixels of the SLM with an input reference beam from a source, wherein the second light beam is a reflection of the input reference beam off the pixels of the SLM, and the pixels are for modulating the reference beam to create the optical phase conjugate.

Block 1808 represents focusing the second beam, or allowing the second light beam to focus, on the sample at the spatial point. The step may further comprise holding, using a sample holder, the sample between the first objective and the second objective, such that the spatial point is on or within the sample, and the first light beam is transmitted through the sample and the second objective before being collected by the DOPC devices.

Block 1810 represents using the first light beam and the second light beam to excite fluorescence from the sample at the spatial point. The step may comprise optimizing fluorescence generated by exciting the sample at the spatial point with the first light beam and the second light beam, by providing the first light beam and the second light beam with a power at the spatial point which is sufficiently low to avoid photobleaching of the sample at the spatial point. The step may comprise performing two photon excitation, wherein a laser that is the source for the input reference beam and a source for the first light beam provides the first light beam and the second light beam with a wavelength such that the fluorescence is generated by two photon excitation of the sample by the first light beam and the second light beam.

The step may further comprise controlling, using a computer processor, a power of the input reference beam so that the second light beam and the first light beam at the spatial point have identical powers as measured by maximum phase contrast in an interference pattern formed at the spatial point between the first light beam and the second light beam, or as measured by the first light beam and the second light beam independently generating an identical fluorescence signal.

Block 1812 represents using the fluorescence to image the sample.

Embodiments of the invention are not limited to the use of an SLM to produce the optical phase conjugate. Any device that may produce an optically phase conjugate the first beam may be used (e.g., a photorefractive crystal). For example, the optical phase conjugating device may digitally produce or create the optical phase conjugate of the first light beam.

Embodiments of the invention are not limited to any particular light beams. The first light beam, the second light beam, and the reference beams, may comprise first light, second light and reference light, respectively, for example.

REFERENCES

The following references are incorporated by reference herein.
1. Chalfie, M., et al., *Green fluorescent protein as a marker for gene-expression*. Science, 1994. 263(5148): p. 802-805.
2. Tsien, R. Y., *The green fluorescent protein*. Annual Review of Biochemistry, 1998. 67: p. 509-544.
3. Hell, S. and E. H. K. Stelzer, *Fundamental improvement of resolution with a 4pi-confocal fluorescence microscope using 2-photon excitation*. Optics Communications, 1992. 93(5-6): p. 277-282.
4. Hell, S. and E. H. K. Stelzer, *Properties of a 4pi confocal fluorescence microscope*. Journal of the Optical Society of America a-Optics Image Science and Vision, 1992. 9(12): p. 2159-2166.
5. Bilenca, A., et al., *Fluorescence coherence tomography*. Optics Express, 2006. 14(16): p. 7134-7143.
6. Yariv, A., *Phase conjugate optics and real-time holography*. Ieee Journal of Quantum Electronics, 1978. 14(9): p. 650-660.
7. Feinberg, J., et al., *Photorefractive effects and light-induced charge migration in barium-titanate*. Journal of Applied Physics, 1980. 51(3): p. 1297-1305.
8. Lind, R. C. and D. G. Steel, *Demonstration of the longitudinal modes and aberration-correction properties of a continuous-wave dye-laser with a phase-conjugate mirror*. Optics Letters, 1981. 6(11): p. 554-556.
9. M. Gower, D. P., *Optical phase conjugation*. 1994, New York: Springer-Verlag.
10. Yaqoob, Z., et al., *Optical phase conjugation for turbidity suppression in biological samples*. Nature Photonics, 2008. 2(2): p. 110-115.
11. McDowell, E. J., et al., *Turbidity suppression from the ballistic to the diffusice regime in biological tissues using optical phase conjugation*. Proceedings of the National Academy of Sciences (submitted), 2009.
12. Yamaguchi, I. and T. Zhang, *Phase-shifting digital holography*. Optics Letters, 1997. 22(16): p. 1268-1270.
13. Cui, X. Q., M. Lew, and C. H. Yang, *Quantitative differential interference contrast microscopy based on structured-aperture interference*. Applied Physics Letters, 2008. 93(9).
14. Supatto, W., et al., *Quantitative imaging of collective cell migration during drosophila gastrulation: Multiphoton microscopy and computational analysis*. Nat. Protocols, 2009. 4(10): p. 1397-1412.
15. S. Hell and E. Stelzer, "Properties of a 4pi confocal fluorescence microscope," *JOSA A*, vol. 9, p. 2159, 1992.
16. Yuan, B. and Y. Liu, *Ultrasound-modulated fluorescence from rhodamine B aqueous solution*. Journal Of Biomedical Optics, 2010. 15: p. 021321.
17. T. J. Dougherty, C. J. Gomer, B. W. Henderson, G. Joni, D. Kessel, M. Korbelik, J. Moan, and Q. Peng, "Photodynamic therapy," *Journal of the National Cancer Institute*, vol. 90, pp. 889-905, June 1998.
18. M. Wenner, "The most transparent research," Nat. Med. 15(10), 1106-1109 (2009).
19. L. V. Wang, "Multiscale photoacoustic microscopy and computed tomography," Nat. Photonics 3(9), 503-509 (2009).
20. I. M. Vellekoop, and A. P. Mosk, "Universal optimal transmission of light through disordered materials," Phys. Rev. Lett. 101(12), 120601 (2008).
21. Z. Yaqoob, D. Psaltis, M. S. Feld, and C. Yang, "Optical phase conjugation for turbidity suppression in biological samples," Nat. Photonics 2(2), 110-115 (2008).
22. I. M. Vellekoop, and A. P. Mosk, "Focusing coherent light through opaque strongly scattering media," Opt. Lett. 32(16), 2309-2311 (2007).
23. I. M. Vellekoop, E. G. van Putten, A. Lagendijk, and A. P. Mosk, "Demixing light paths inside disordered metamaterials," Opt. Express 16(1), 67-80 (2008).
24. M. Cui, E. J. McDowell, and C. H. Yang, "Observation of polarization-gate based reconstruction quality improvement during the process of turbidity suppression by optical phase conjugation," Appl. Phys. Lett. 95(12), 123702 (2009).
25. M. Cui, E. J. McDowell, and C. Yang, "An in vivo study of turbidity suppression by optical phase conjugation (tsopc) on rabbit ear," Opt. Express 18(1), 25-30 (2010).
26. A. Yariv, and P. Yeh, "Phase conjugate optics and real-time holography," IEEE J. Quantum Electron. 14(9), 650-660 (1978).
27. J. Feinberg, and R. W. Hellwarth, "Phase-conjugating mirror with continuous-wave gain," Opt. Lett. 5(12), 519-521 (1980).
28. R. C. Lind, and D. G. Steel, "Demonstration of the longitudinal modes and aberrationcorrection properties of a continuous-wave dye laser with a phase-conjugate mirror," Opt. Lett. 6(11), 554-556 (1981).
29. I. Lindsay, "Specular reflection cancellation enhancement in the presence of a phase-conjugate mirror," J. Opt. Soc. Am. B 4(11), 1810-1815 (1987).
30. D. M. Pepper, "Observation of diminished specular reflectivity from phase-conjugate mirrors," Phys. Rev. Lett. 62(25), 2945-2948 (1989).
31. P. Yeh, Introduction to photorefractive nonlinear optics (John Wiley & Sons, Inc, New York, 1993).
32. D. P. M. Gower, Optical phase conjugation (Springer-Verlag, New York, 1994).
33. C. A. Primmerman, D. V. Murphy, D. A. Page, B. G. Zollars, and H. T. Barclay, "Compensation of atmospheric optical distortion using a synthetic beacon," Nature 353 (6340), 141-143 (1991).
34. M. J. Booth, M. A. A. Neil, R. Juskaitis, and T. Wilson, "Adaptive aberration correction in a confocal microscope," Proc. Natl. Acad. Sci. U.S.A. 99(9), 5788-5792 (2002).
35. M. Rueckel, J. A. Mack-Bucher, and W. Denk, "Adaptive wavefront correction in two-photon microscopy using coherence-gated wavefront sensing," Proc. Natl. Acad. Sci. U.S.A. 103(46), 17137-17142 (2006).
36. D. Débarre, E. J. Botcherby, T. Watanabe, S. Srinivas, M. J. Booth, and T. Wilson, "Image-based adaptive optics for two-photon microscopy," Opt. Lett. 34(16), 2495-2497 (2009).
37. D. Débarre, E. J. Botcherby, M. J. Booth, and T. Wilson, "Adaptive optics for structured illumination microscopy," Opt. Express 16(13), 9290-9305 (2008).
38. Z. Yaqoob, D. Psaltis, M. S. Feld, and C. Yang, "Optical phase conjugation for turbidity suppression in biological samples" *Nature Photonics*, vol. 2, pp. 110-115, 2008.
39. M. Cui, E. McDowell, and C. Yang, "Observation of polarization-gate based reconstruction quality improvement during the process of turbidity suppression by optical phase conjugation," *Applied Physics Letters*, vol. 95, p. 123702, 2009.
40. E. N. Leith and J. Upatnieks, "Holographic imagery through diffusing media," *JOSA*, vol. 56, p. 523, 1966.
41. M. Wenner, "The most transparent research," *Nature Medicine*, vol. 15, p. 1106, 2009.

42. T. Vo-Dinh, *Biomedical Photonics Handbook*. Boca Raton, Fla.: CRC Press, 2003.
43. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical Coherence Tomography," *Science*, vol. 254, pp. 1178-1181, Nov. 22, 1991.
44. D. A. Boas, D. H. Brooks, E. L. Miller, C. A. DiMarzio, M. Kilmer, R. J. Gaudette, and Q. Zhang, "Imaging the body with diffuse optical tomography," *IEEE Signal Processing*, vol. 18, pp. 57-75, 2001.
45. E. Jakeman and K. D. Ridley, "Incomplete phase conjugation through a random phase screen. II. Numerical simulations," *JOSA A*, vol. 13, p. 2293, 1996.
46. S. C. W. Hyde, R. Jones, N. P. Barry, J. C. Dainty, P. M. W. French, K. M. Kwolek, D. D. Nolte, and M. R. Melloch, "Depth-resolved holography through turbid media using photorefraction," *IEEE JSTQE*, vol. 2, pp. 965-975, 1996.
47. I. Vellokoop and A. Mosk, "Universal Optimal Transmission of Light Through Disordered Materials," *Phys. Rev. Lett.*, vol. 101, p. 120601, 2008.
48. M. Fink, "Time-reversed acoustics," *Scientific American*, vol. 281, pp. 91-97, November 1999.
49. S. Hell and E. Stelzer, "Properties of a 4pi confocal fluorescence microscope.," *JOSA A*, vol. 9, p. 2159, 1992.
50. L. Wang and X. Zhao, "Ultrasound-modulated optical tomography of absorbing objects buried in dense tissue-simulating turbid media," *Applied Optics*, vol. 36, p. 7277, 1997.
51. T. J. Dougherty, C. J. Gomer, B. W. Henderson, G. Joni, D. Kessel, M. Korbelik, J. Moan, and Q. Peng, "Photodynamic therapy," *Journal of the National Cancer Institute*, vol. 90, pp. 889-905, June 1998.
52. X. Cui, L. M. Lee, X. Heng, W. Zhong, P. W. Sternberg, D. Psaltis, and C. Yang, "Lensless high-resolution on-chip optofluidic microscopes for *Caenorhabditis elegans* and cell imaging," *PNAS*, vol. 105, p. 10670, 2008.
54. E. Check Hayden, "Microscopic marvels: Microscope for the masses," *Nature*, vol. 459, p. 632, 2009.
55. M. Fink, "Time reversed acoustics," Phys. Today 50(3), 34-40 (1997).
56. M. Fink, "Time-reversed acoustics," Sci. Am. 281(5), 91-97 (1999).
57. I. Yamaguchi, and T. Zhang, "Phase-shifting digital holography," Opt. Lett. 22(16), 1268-1270 (1997).
58. T. Zhang, and I. Yamaguchi, "Three-dimensional microscopy with phase-shifting digital holography," Opt. Lett. 23(15), 1221-1223 (1998).
59. A. Derode, A. Tourin, and M. Fink, "Random multiple scattering of ultrasound. Ii. Is time reversal a self-averaging process?" Phys. Rev. E Stat. Nonlin. Soft Matter Phys. 64(3), 036606 (2001).
60. J. W. Goodman, "Some fundamental properties of speckle," J. Opt. Soc. Am. 66(11), 1145-1150 (1976).
61. Y. Kawata et. al, "4-Pi confocal optical system with phase conjugation," Optics letters, Vol. 21. No. 18, pages 1415-1417, Sep. 15, 1996.
62. Meng Cui and Changhuei Yang, "Implementation of a digital optical phase conjugation system and its application to study the robustness of turbidity suppression by phase conjugation," Optics Express, Vol. 18, No. 4, published 2 Feb. 2010.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A 4-Pi microscope, comprising:
   (a) a first objective for focusing a first light beam on a sample at a spatial point;
   (b) one or more Digital Optical Phase Conjugation (DOPC) devices, wherein the DOPC devices each include:
      (i) a sensor for detecting the first light beam that has been transmitted through the sample and inputted on the sensor; and
      (ii) a spatial light modulator (SLM) for outputting, in response to the sensor detecting the first light beam, a second light beam that is an optical phase conjugate of the first light beam; and
   (c) a second objective positioned to transmit the first light beam to the sensor and focus the second light beam on the sample at the spatial point, so that the first light beam and the second light beam are counter-propagating and both focused to the spatial point.

2. The microscope of claim 1, further comprising a sample holder, between the first objective and the second objective, for holding the sample such that the spatial point is on or within the sample, and the first light beam is transmitted through the sample and the second objective before being collected by the DOPC devices.

3. The microscope of claim 1, further comprising a source of an input reference beam, positioned to illuminate one or more pixels of the SLM, wherein the second light beam is a reflection of the input reference beam off the pixels of the SLM, and the pixels are for modulating the reference beam to create the optical phase conjugate.

4. The microscope of claim 3, further comprising:
   a beam splitter positioned to combine the first light beam and a sensor reference beam, on the sensor so that the first light beam and the sensor reference beam interfere on the sensor and form one or more holograms on the sensor, the holograms including interferometric data;
   one or more processors for:
      (1) receiving the interferometric data and determining one or more phases and one or more amplitudes of first light fields of the first light beam from the interferometric data,
      (2) digitally modifying the phases and the amplitudes to produce one or more modified phases and one or more modified amplitudes, and
      (3) outputting the modified phases and modified amplitudes to the SLM so that the SLM outputs the second light beam having the modified phases and modified amplitudes that are the optical phase conjugates of the phases and the amplitudes.

5. The microscope of claim 4, further comprising an electro-optic modulator positioned to control a relative phase between the first light beam and the sensor reference beam, so that the holograms include one or more phase shifted holograms.

6. The microscope of claim 3, further comprising:
   a computer processor for controlling a power of the input reference beam so that the second light beam and the first light beam at the spatial point have identical powers as measured by maximum phase contrast in an interference pattern formed at the spatial point between the first light beam and the second light beam, or as measured by the first light beam and the second light beam independently generating an identical fluorescence signal.

7. The microscope of claim 6, wherein the first light beam and the second light beam have a power at the spatial point which is sufficiently low to avoid photobleaching of the sample at the spatial point, thereby optimizing fluorescence generated by exciting the sample at the spatial point with the first light beam and the second light beam.

8. The microscope of claim 6, further comprising a laser that is the source for the input reference beam and a source for the first light beam, wherein the first light beam and the second light beam have a wavelength such that the fluorescence is generated by two photon excitation of the sample by the first light beam and the second light beam.

9. The microscope of claim 1, further comprising a detector positioned for imaging fluorescence of the sample generated by the first light beam and the second light beam.

10. The microscope of claim 1, wherein the DOPC devices each have a response time or update speed of at least 1 KHz or faster than movements in living tissues that deteriorate Turbidity Suppression by Optical Phase Conjugation (TSOPC) reconstruction efficiency.

11. A method for imaging using a 4-Pi Microscope, comprising:
focusing a first light beam at a spatial point on a sample;
detecting the first light beam that has been transmitted through the sample;
outputting, using a spatial light modulator (SLM), a second light beam that is an optical phase conjugate of the first light beam, wherein the first light beam and the second light beam are counter propagating and the second light beam retraces a path of the first light beam, thereby automatically aligning the 4-pi microscope;
focusing the second light beam, or allowing the second light beam to focus, on the sample at the spatial point;
using the first light beam and the second light beam to excite fluorescence from the sample at the spatial point; and
using the fluorescence to image the sample.

12. The method of claim 11, wherein the focusing of the first light beam is with a first objective, the method further comprising:
transmitting the first light beam through a second objective to a sensor;
detecting, on the sensor, the first light beam that has been transmitted through the sample and inputted on the sensor; wherein the SLM outputs the second light beam in response to the first light beam detected by the sensor and the SLM and the sensor are each included in one or more Digital Optical Phase Conjugation (DOPC) devices; and
focusing the second light beam on the sample at the spatial point, so that the first light beam and the second light beam are counter-propagating and both focused to the spatial point.

13. The microscope of claim 12, wherein the DOPC devices each have a response time or update speed of at least 1 KHz or faster than movements in living tissues that deteriorate Turbidity Suppression by Optical Phase Conjugation (TSOPC) reconstruction efficiency.

14. The method of claim 11, further comprising:
holding, using a sample holder, the sample between the first objective and the second objective, such that the spatial point is on or within the sample, and the first light beam is transmitted through the sample and the second objective before being collected by the DOPC devices.

15. The method of claim 14, further comprising:
illuminating one or more pixels of the SLM with an input reference beam from a source, wherein the second light beam is a reflection of the input reference beam off the pixels of the SLM, and the pixels are for modulating the reference beam to create the optical phase conjugate.

16. The method of claim 15, further comprising:
combining, using a beamsplitter, the first light beam and the sensor reference beam, onto the sensor so that the first light beam and the sensor reference beam interfere on the sensor and form one or more holograms on the sensor, the holograms including interferometric data;
receiving, in one or more processors, the interferometric data and determining one or more phases and one or more amplitudes of first light fields of the first light beam from the interferometric data;
digitally modifying, in the one or more processors, the phases and the amplitudes to produce one or more modified phases and one or more modified amplitudes, and
outputting, from the one or more processors, the modified phases and modified amplitudes to the SLM so that the SLM outputs the second light beam having the modified phases and modified amplitudes that are the optical phase conjugates of the phases and the amplitudes.

17. The method of claim 16, further comprising:
controlling, using an electro-optic modulator, a relative phase between the first light beam and the sensor reference beam, so that the holograms include one or more phase shifted holograms.

18. The method of claim 15, further comprising:
controlling, using a computer processor, a power of the input reference beam so that the second light beam and the first light beam at the spatial point have identical powers as measured by maximum phase contrast in an interference pattern formed at the spatial point between the first light beam and the second light beam, or as measured by the first light beam and the second light beam independently generating an identical fluorescence signal.

19. The method of claim 18, further comprising:
optimizing fluorescence generated by exciting the sample at the spatial point with the first light beam and the second light beam, by providing the first light beam and the second light beam with a power at the spatial point which is sufficiently low to avoid photobleaching of the sample at the spatial point.

20. The method of claim 15, further comprising
performing two photon excitation of the sample at the spatial point using a laser that is the source for the input reference beam and a source for the first light beam, wherein the first light beam and the second light beam have a wavelength such that the fluorescence is generated by two photon excitation of the sample by the first light beam and the second light beam.

21. A method for assembling a 4-Pi microscope, comprising:
(a) positioning:
(i) a first objective for focusing a first light beam on a sample at a spatial point;
(ii) one or more Digital Optical Phase Conjugation (DOPC) devices, wherein the DOPC devices each include:
(1) a sensor for detecting the first light beam that has been transmitted through the sample and inputted on the sensor; and
(2) a spatial light modulator (SLM) for outputting, in response to the sensor detecting the first light beam, a second light beam that is an optical phase conjugate of the first light beam; and (iii) a second objective positioned to transmit the first light beam to the sensor and focus the second light beam on the sample at the spatial point, so that the first light beam and the second light beam are counter-propagating and both focused to the spatial point.

* * * * *

UNITED STATES PATENT AND TRADEMARK OFFICE
CERTIFICATE OF CORRECTION

PATENT NO.       : 8,830,573 B2  
APPLICATION NO.  : 12/943818  
DATED            : September 9, 2014  
INVENTOR(S)      : Cui et al.

Page 1 of 1

It is certified that error appears in the above-identified patent and that said Letters Patent is hereby corrected as shown below:

In the Specification

Column 2

Line 19, after header titled CROSS-REFERENCE TO RELATED APPLICATIONS and before header titled BACKGROUND OF THE INVENTION, please insert the following:

--STATEMENT REGARDING FEDERALLY SPONSORED RESEARCH AND DEVELOPMENT

This invention was made with government support under Grant No. EB008866 awarded by the National Institutes of Health. The government has certain rights in the invention.--

Signed and Sealed this  
Sixteenth Day of December, 2014

Michelle K. Lee  
*Deputy Director of the United States Patent and Trademark Office*